US012465727B2

(12) United States Patent
Burkholz et al.

(10) Patent No.: US 12,465,727 B2
(45) Date of Patent: Nov. 11, 2025

(54) CLOSED IV ACCESS DEVICE WITH PADDLE GRIP NEEDLE HUB AND FLASH CHAMBER

(71) Applicant: Becton, Dickinson and Company, Franklin Lakes, NJ (US)

(72) Inventors: Jonathan Karl Burkholz, Salt Lake City, UT (US); Bart D. Peterson, Farmington, UT (US); Bin Wang, Irvine, CA (US); Ralph L. Sonderegger, Farmington, UT (US); Tyler Warner, Bluffdale, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 18/237,328

(22) Filed: Aug. 23, 2023

(65) Prior Publication Data

US 2023/0390533 A1 Dec. 7, 2023

Related U.S. Application Data

(63) Continuation of application No. 16/833,058, filed on Mar. 27, 2020, now Pat. No. 11,786,703, which is a (Continued)

(51) Int. Cl.
*A61M 25/06* (2006.01)

(52) U.S. Cl.
CPC .... *A61M 25/0693* (2013.01); *A61M 25/0606* (2013.01); *A61M 25/0637* (2013.01)

(58) Field of Classification Search
CPC .......... A61M 25/0693; A61M 25/0606; A61M 25/0637

(Continued)

(56) References Cited

U.S. PATENT DOCUMENTS 3,046,984 A 7/1962 Eby
3,547,119 A 12/1970 Hall et al.

(Continued)

FOREIGN PATENT DOCUMENTS

AU 2016344417 B2 5/2019
AU 2019216675 B2 9/2020

(Continued)

OTHER PUBLICATIONS

Address Multi-Drug Resistant Organisms on the Skin with Early Preop Prep, Sage Products, Inc., Retrieved from the nternet URL: http://www.sageproducts.com/products/ssi-prevention.cfm, on Oct. 31, 2008, p. 1.

(Continued)

*Primary Examiner* — Phillip A Gray

(74) *Attorney, Agent, or Firm* — Kirton McConkie; Whitney Blair; Kevin Stinger

(57) ABSTRACT

An IV access device can include a needle hub that incorporates a flash chamber. The flash chamber can be used to provide visual confirmation of proper catheter placement within a vein. The flash chamber can include a path-defining structure to facilitate identifying whether blood is continually flowing into the flash chamber. The flash chamber may also be removable from the needle hub. In some cases, the needle hub may include a paddle grip that facilitates insertion of the catheter and separation of the needle hub from the catheter adapter.

6 Claims, 13 Drawing Sheets

Related U.S. Application Data continuation of application No. 15/286,188, filed on Oct. 5, 2016, now Pat. No. 10,639,455.

(60) Provisional application No. 62/296,385, filed on Feb. 17, 2016, provisional application No. 62/296,383, filed on Feb. 17, 2016, provisional application No. 62/247,596, filed on Oct. 28, 2015, provisional application No. 62/247,617, filed on Oct. 28, 2015, provisional application No. 62/247,607, filed on Oct. 28, 2015, provisional application No. 62/247,626, filed on Oct. 28, 2015, provisional application No. 62/247,624, filed on Oct. 28, 2015, provisional application No. 62/247,621, filed on Oct. 28, 2015, provisional application No. 62/247,599, filed on Oct. 28, 2015.

(58) Field of Classification Search
USPC .................................................... 604/168.01
See application file for complete search history.

(56) References Cited

U.S. PATENT DOCUMENTS 3,589,361 A 6/1971 Loper et al.
3,827,434 A 8/1974 Thompson et al.
3,853,127 A 12/1974 Spademan
3,859,998 A 1/1975 Thomas et al.
4,003,403 A 1/1977 Nehring
4,043,346 A 8/1977 Mobley et al.
4,099,528 A 7/1978 Sorenson et al.
4,106,491 A 8/1978 Guerra
4,149,539 A 4/1979 Cianci
4,172,448 A 10/1979 Brush
4,177,809 A 12/1979 Moorehead
4,193,399 A 3/1980 Robinson
4,200,096 A 4/1980 Charvin
4,269,186 A 5/1981 Loveless et al.
4,311,137 A * 1/1982 Gerard ............. A61M 25/0606 604/122
4,317,445 A 3/1982 Robinson
4,326,519 A 4/1982 D'Alo et al.
4,353,369 A 10/1982 Muetterties et al.
4,362,156 A 12/1982 Feller, Jr. et al.
4,365,630 A 12/1982 McFarlane
4,387,879 A 6/1983 Tauschinski
4,419,094 A 12/1983 Patel
4,445,893 A 5/1984 Bodicky
4,449,693 A 5/1984 Gereg
4,496,348 A 1/1985 Genese et al.
4,525,157 A 6/1985 Vaillancourt
4,531,935 A 7/1985 Berryessa
4,531,937 A * 7/1985 Yates ............... A61M 25/0097 604/122
4,682,980 A 7/1987 Suzuki
4,701,162 A 10/1987 Rosenberg
4,703,761 A 11/1987 Rathbone et al.
4,710,173 A 12/1987 McFarlane
4,758,225 A 7/1988 Cox et al.
4,765,588 A 8/1988 Atkinson
4,767,408 A 8/1988 McFarlane
4,772,264 A 9/1988 Cragg
4,813,939 A 3/1989 Marcus
4,834,708 A 5/1989 Pillari
4,842,591 A 6/1989 Luther
4,874,377 A 10/1989 Newgard et al.
4,894,052 A 1/1990 Crawford
4,917,668 A 4/1990 Haindl
4,917,671 A 4/1990 Chang
4,925,444 A 5/1990 Orkin et al.
4,935,010 A 6/1990 Cox et al.
4,950,257 A 8/1990 Hibbs et al.
4,966,586 A 10/1990 Vaillancourt
5,007,898 A 4/1991 Rosenbluth et al.
5,032,116 A 7/1991 Peterson et al.
5,041,097 A 8/1991 Johnson
5,053,014 A 10/1991 Van Heugten
5,057,087 A 10/1991 Harmon
5,059,186 A 10/1991 Yamamoto et al.
5,062,836 A 11/1991 Wendell
5,064,416 A 11/1991 Newgard et al.
5,084,023 A 1/1992 Lemieux
5,085,645 A 2/1992 Purdy et al.
5,108,374 A 4/1992 Lemieux
5,127,905 A 7/1992 Lemieux
5,135,504 A 8/1992 McLees
5,154,703 A 10/1992 Bonaldo
5,156,596 A 10/1992 Balbierz et al.
5,176,653 A 1/1993 Metais
5,176,662 A 1/1993 Bartholomew et al.
5,186,712 A 2/1993 Kelso et al.
5,201,717 A 4/1993 Wyatt et al.
5,211,634 A 5/1993 Vaillancourt
5,215,525 A 6/1993 Sturman
5,215,528 A 6/1993 Purdy et al.
5,215,529 A 6/1993 Fields et al.
5,226,883 A 7/1993 Katsaros et al.
5,234,410 A 8/1993 Graham et al.
5,242,411 A 9/1993 Yamamoto et al.
5,269,764 A 12/1993 Vetter et al.
5,295,969 A 3/1994 Fischell et al.
5,300,045 A 4/1994 Plassche, Jr. et al.
5,306,243 A 4/1994 Bonaldo
5,330,435 A 7/1994 Vaillancourt
5,354,281 A 10/1994 Chen
5,456,675 A 10/1995 wolbring et al.
5,487,728 A 1/1996 Vaillancourt
5,498,241 A 3/1996 Fabozzi
5,509,912 A 4/1996 Vaillancourt et al.
5,520,666 A 5/1996 Choudhury et al.
5,549,566 A 8/1996 Elias et al.
5,549,576 A 8/1996 Patterson et al.
5,549,577 A 8/1996 Siegel et al.
5,562,631 A 10/1996 Bogert
5,573,510 A 11/1996 Isaacson
5,575,769 A 11/1996 Vaillancourt
5,589,120 A 12/1996 Khan et al.
5,599,310 A 2/1997 Bogert
5,601,536 A 2/1997 Crawford et al.
5,613,663 A 3/1997 Schmidt et al.
5,651,772 A 7/1997 Arnett
5,657,963 A 8/1997 Hinchliffe et al.
5,690,612 A 11/1997 Lopez et al.
5,690,619 A 11/1997 Erskine
5,697,907 A 12/1997 Gaba
5,697,914 A 12/1997 Brimhall
5,697,915 A 12/1997 Lynn
5,738,144 A 4/1998 Rogers
5,749,861 A 5/1998 Guala et al.
5,772,636 A 6/1998 Brimhall et al.
5,800,399 A 9/1998 Bogert et al.
5,806,831 A 9/1998 Paradis
5,810,835 A 9/1998 Ryan et al.
5,817,069 A 10/1998 Arnett
5,853,393 A 12/1998 Bogert
5,882,345 A 3/1999 Yoon
5,911,710 A 6/1999 Barry et al.
5,935,109 A 8/1999 Donnan
5,935,110 A 8/1999 Brimhall
5,947,932 A 9/1999 Desecki et al.
5,954,698 A 9/1999 Pike
5,961,497 A 10/1999 Larkin
5,967,490 A 10/1999 Pike
6,039,302 A 3/2000 Cote, Sr. et al.
6,056,726 A 5/2000 Isaacson
6,077,244 A 6/2000 Botich et al.
6,117,108 A 9/2000 Woehr et al.
6,142,981 A 11/2000 Heck et al.
6,156,010 A 12/2000 Kuracina et al.
6,171,287 B1 1/2001 Lynn et al.
6,206,851 B1 3/2001 Prosl
6,217,566 B1 4/2001 Ju et al.
6,221,047 B1 4/2001 Greene et al.

(56) References Cited

U.S. PATENT DOCUMENTS

| | | | | |
|---|---|---|---|---|
| 6,224,569 | B1 | 5/2001 | Brimhall | |
| 6,273,869 | B1 | 8/2001 | Vaillancourt | |
| 6,287,278 | B1 | 9/2001 | Woehr et al. | |
| 6,379,332 | B1 | 4/2002 | Van Landuyt | |
| 6,387,075 | B1 | 5/2002 | Stivland et al. | |
| 6,394,983 | B1 | 5/2002 | Mayoral et al. | |
| 6,440,119 | B1 | 8/2002 | Nakada et al. | |
| 6,461,362 | B1 | 10/2002 | Halseth et al. | |
| 6,485,473 | B1 | 11/2002 | Lynn | |
| 6,497,994 | B1 * | 12/2002 | Kafrawy | G03F 7/00 430/323 |
| 6,506,181 | B2 | 1/2003 | Meng et al. | |
| 6,565,542 | B2 | 5/2003 | Kumar et al. | |
| 6,575,960 | B2 | 6/2003 | Becker et al. | |
| 6,595,954 | B1 | 7/2003 | Luther et al. | |
| 6,595,981 | B2 | 7/2003 | Huet | |
| 6,616,630 | B1 | 9/2003 | Woehr et al. | |
| 6,652,486 | B2 | 11/2003 | Bialecki et al. | |
| 6,663,592 | B2 | 12/2003 | Rhad et al. | |
| 6,689,102 | B2 | 2/2004 | Greene | |
| 6,695,814 | B2 | 2/2004 | Greene et al. | |
| 6,699,221 | B2 | 3/2004 | Vaillancourt | |
| 6,709,419 | B2 | 3/2004 | Woehr | |
| 6,719,726 | B2 | 4/2004 | Meng et al. | |
| 6,740,063 | B2 | 5/2004 | Lynn | |
| 6,837,884 | B2 | 1/2005 | Woloszko | |
| 6,883,778 | B1 | 4/2005 | Newton et al. | |
| 7,008,404 | B2 | 3/2006 | Nakajima | |
| 7,347,839 | B2 | 3/2008 | Hiejima | |
| 7,396,346 | B2 | 7/2008 | Nakajima | |
| 7,470,254 | B2 | 12/2008 | Basta et al. | |
| 7,670,317 | B2 | 3/2010 | Cindrich et al. | |
| 7,694,403 | B2 | 4/2010 | Moulton | |
| 7,736,339 | B2 | 6/2010 | Woehr et al. | |
| 7,914,494 | B2 | 3/2011 | Hiejima | |
| 8,066,670 | B2 | 11/2011 | Cluff et al. | |
| 8,066,675 | B2 | 11/2011 | Cindrich et al. | |
| 8,070,725 | B2 | 12/2011 | Christensen | |
| 8,357,119 | B2 | 1/2013 | Stout et al. | |
| 8,361,020 | B2 | 1/2013 | Stout et al. | |
| 8,388,583 | B2 | 3/2013 | Stout et al. | |
| 8,574,203 | B2 | 11/2013 | Stout et al. | |
| 8,591,473 | B2 | 11/2013 | Jones et al. | |
| 8,597,252 | B2 | 12/2013 | Burkholz et al. | |
| 8,641,675 | B2 | 2/2014 | Stout et al. | |
| 8,679,063 | B2 | 3/2014 | Stout et al. | |
| 8,702,658 | B2 | 4/2014 | Spearman | |
| 10,245,416 | B2 | 4/2019 | Harding et al. | |
| 10,525,237 | B2 | 1/2020 | Burkholz et al. | |
| 10,549,073 | B2 | 2/2020 | Burkholz et al. | |
| 10,639,455 | B2 | 5/2020 | Burkholz et al. | |
| 10,744,305 | B2 | 8/2020 | Burkholz et al. | |
| 10,814,106 | B2 | 10/2020 | Garrison et al. | |
| 11,571,551 | B2 | 2/2023 | Burkholz et al. | |
| 12,257,405 | B2 | 3/2025 | Burkholz et al. | |
| 2001/0053895 | A1 | 12/2001 | Vaillancourt | |
| 2002/0082546 | A1 | 6/2002 | Crank et al. | |
| 2002/0177814 | A1 | 11/2002 | Meng et al. | |
| 2003/0208165 | A1 | 11/2003 | Christensen et al. | |
| 2004/0078003 | A1 | 4/2004 | Smith et al. | |
| 2004/0181192 | A1 | 9/2004 | Cuppy | |
| 2005/0015071 | A1 | 1/2005 | Brimhall | |
| 2005/0251092 | A1 | 11/2005 | Howell et al. | |
| 2005/0277879 | A1 | 12/2005 | Daga | |
| 2006/0129064 | A1 | 6/2006 | Conway et al. | |
| 2006/0163515 | A1 | 7/2006 | Ruschke | |
| 2006/0264833 | A1 | 11/2006 | Moulton | |
| 2007/0008826 | A1 | 1/2007 | Hung | |
| 2007/0010796 | A1 | 1/2007 | Moran et al. | |
| 2007/0043334 | A1 | 2/2007 | Guala | |
| 2007/0083157 | A1 | 4/2007 | Belley et al. | |
| 2007/0083162 | A1 | 4/2007 | O'Reagan et al. | |
| 2007/0225648 | A1 | 9/2007 | Winsor et al. | |
| 2007/0270758 | A1 | 11/2007 | Hanner et al. | |
| 2008/0039796 | A1 | 2/2008 | Nakajima | |
| 2008/0103449 | A1 | 5/2008 | Murashita et al. | |
| 2008/0108944 | A1 | 5/2008 | Woehr et al. | |
| 2008/0167577 | A1 | 7/2008 | Weilbacher et al. | |
| 2009/0054845 | A1 | 2/2009 | Puhasmagi et al. | |
| 2009/0099431 | A1 | 4/2009 | Dalebout et al. | |
| 2010/0168675 | A1 | 7/2010 | Cindrich et al. | |
| 2010/0168827 | A1 | 7/2010 | Schultz | |
| 2010/0204648 | A1 | 8/2010 | Stout et al. | |
| 2010/0204652 | A1 | 8/2010 | Morrissey et al. | |
| 2010/0204675 | A1 | 8/2010 | Woehr et al. | |
| 2010/0222746 | A1 | 9/2010 | Burkholz | |
| 2010/0280455 | A1 | 11/2010 | Ogawa et al. | |
| 2011/0046570 | A1 | 2/2011 | Stout et al. | |
| 2011/0054403 | A1 | 3/2011 | Tanabe et al. | |
| 2011/0130728 | A1 | 6/2011 | McKinnon | |
| 2012/0016265 | A1 | 1/2012 | Peterson et al. | |
| 2012/0016307 | A1 | 1/2012 | Burkholz et al. | |
| 2012/0053523 | A1 | 3/2012 | Harding | |
| 2013/0090608 | A1 | 4/2013 | Stout et al. | |
| 2013/0150793 | A1 | 6/2013 | Beissel et al. | |
| 2013/0218082 | A1 | 8/2013 | Hyer et al. | |
| 2013/0237925 | A1 | 9/2013 | Trainer et al. | |
| 2014/0107584 | A1 | 4/2014 | Rosenberg et al. | |
| 2014/0364809 | A1 | 12/2014 | Isaacson et al. | |
| 2017/0080205 | A1 | 3/2017 | Lauer | |
| 2017/0120008 | A1 | 5/2017 | Burkholz et al. | |
| 2017/0120009 | A1 | 5/2017 | Garrison et al. | |
| 2017/0120014 | A1 | 5/2017 | Harding et al. | |
| 2017/0216535 | A1 | 8/2017 | Mao | |
| 2017/0347913 | A1 | 12/2017 | Isaacson et al. | |

FOREIGN PATENT DOCUMENTS

| | | | |
|---|---|---|---|
| CA | 2133053 | A1 | 3/1995 |
| CA | 2914701 | A1 | 12/2014 |
| CA | 3002701 | A1 | 5/2017 |
| CA | 3096888 | C | 10/2022 |
| CN | 1184677 | A | 6/1998 |
| CN | 101321549 | A | 12/2008 |
| CN | 101353545 | A | 1/2009 |
| CN | 101448543 | A | 6/2009 |
| CN | 201798996 | U | 4/2011 |
| CN | 102143774 | A | 8/2011 |
| CN | 102355924 | A | 2/2012 |
| CN | 102802716 | A | 11/2012 |
| CN | 103068434 | A | 4/2013 |
| CN | 202909200 | U | 5/2013 |
| CN | 203154451 | U | 8/2013 |
| CN | 203852671 | U | 10/2014 |
| CN | 104411358 | A | 3/2015 |
| CN | 206652048 | U | 11/2017 |
| CN | 206652049 | U | 11/2017 |
| DE | 3834600 | C1 | 12/1989 |
| DE | 202009009602 | U1 | 12/2009 |
| EP | 0036294 | A2 | 9/1981 |
| EP | 0070087 | A1 | 1/1983 |
| EP | 0139872 | A1 | 5/1985 |
| EP | 1016429 | A1 | 7/2000 |
| EP | 1679043 | B1 | 7/2006 |
| EP | 1884257 | A1 | 2/2008 |
| EP | 1944049 | A1 | 7/2008 |
| EP | 2022421 | A1 | 2/2009 |
| EP | 2044970 | A1 | 4/2009 |
| EP | 2327434 | A1 | 6/2011 |
| EP | 3368118 | A2 | 9/2018 |
| EP | 3669925 | A1 | 6/2020 |
| EP | 3368127 | B1 | 7/2020 |
| GB | 2508466 | A | 10/2014 |
| JP | 3188771 | B2 | 7/2001 |
| JP | 2001514943 | A | 9/2001 |
| JP | 2004528127 | A | 9/2004 |
| JP | 2005523782 | A | 8/2005 |
| JP | 2005526526 | A | 9/2005 |
| JP | 2006019580 | A | 1/2006 |
| JP | 2008097955 | A | 4/2008 |
| JP | 2011045544 | A | 3/2011 |
| JP | 2012521797 | A | 9/2012 |
| JP | 2012200425 | A | 10/2012 |
| JP | 2014108112 | A | 6/2014 |

(56) References Cited

FOREIGN PATENT DOCUMENTS

| | | | |
|---|---|---|---|
| JP | 2018532012 | A | 11/2018 |
| JP | 6877421 | B2 | 5/2021 |
| MX | 2018004611 | A | 8/2018 |
| WO | 8807388 | A1 | 10/1988 |
| WO | 9842393 | A1 | 10/1998 |
| WO | 9934849 | A1 | 7/1999 |
| WO | 0012171 | A1 | 3/2000 |
| WO | 0066189 | A2 | 11/2000 |
| WO | 0074743 | A1 | 12/2000 |
| WO | 0112254 | A1 | 2/2001 |
| WO | 0147592 | A1 | 7/2001 |
| WO | 0195862 | A1 | 12/2001 |
| WO | 02051464 | A2 | 7/2002 |
| WO | 2002096494 | A1 | 12/2002 |
| WO | 2002096495 | A2 | 12/2002 |
| WO | 2004082727 | A1 | 9/2004 |
| WO | 2004087247 | A2 | 10/2004 |
| WO | 2004098685 | A1 | 11/2004 |
| WO | 2006027923 | A1 | 3/2006 |
| WO | 2006037638 | A1 | 4/2006 |
| WO | 2007052655 | A1 | 5/2007 |
| WO | 2008022258 | A2 | 2/2008 |
| WO | 2008045761 | A2 | 4/2008 |
| WO | 2008052790 | A2 | 5/2008 |
| WO | 2008058132 | A2 | 5/2008 |
| WO | 2008058133 | A2 | 5/2008 |
| WO | 2009114833 | A1 | 9/2009 |
| WO | 2010093791 | A1 | 8/2010 |
| WO | 2010111283 | A1 | 9/2010 |
| WO | 2010111285 | A1 | 9/2010 |
| WO | 2011055287 | A2 | 5/2011 |
| WO | 2011109542 | A1 | 9/2011 |
| WO | 2012020633 | A1 | 2/2012 |
| WO | 2015161299 | A1 | 10/2015 |
| WO | 2016007442 | A1 | 1/2016 |
| WO | 2016152169 | A1 | 9/2016 |
| WO | 2017062579 | A1 | 4/2017 |
| WO | 2017074685 | A2 | 5/2017 |

OTHER PUBLICATIONS

ChloraPrep, Enturia, Retrieved from the internet URL: http://www. enturia. com/products/chloraPrep/chloraPrepproduct. html, on Oct. 31, 2008, p. 1-3.

Clinell Alcoholic 2% Chlorhexidine, Gama Healthcare, Retrieved from the internet URL: http://www.gamahealthcare.m/clinellaca2c. html, on Nov. 7, 2008, p. 1-3.

ComfortCoat Hydrophilic Coating, DSM in Medical, Retrieved from the internet URL: http://www.dsm.com/en_US/medical/public/home/pages/product-coating-comfortcoat.jsp, updated Jan. 11, 2013, on Apr. 22, 2013.

Lubricent-Lubricious Hydrophilic Coatings for Medical Devices, Harland Medical Systems, Retrieved from the Internet URL= http://www.harlandmedical.com/index.phpimaterialsilubricenthtml, on Apr. 22, 2013, p. 1-2.

Preoperative Skin Preparation and Peri operative Oral Care for the Short-Term Ventilated Patient, Sage Products, Inc., Retrieved from the intemet URL: http://www.sageproducts.com/productsissi-vap-prevention.cfm, on Oct. 31, 2008, p. 1.

Preoperative Skin Preparation for the Surgical Patient, Sage Products, Inc., Retrieved from the internet URL: http:/1 www.sageproducts. com/products/skin-prep.cfm, on Oct. 31, 2008, p. 1.

UV & EB Cure, Xiper Innovations, Inc., Retrieved from the intemet URL: http://xiperinnovations.com/uv-eb-cure, on Mar. 16, 2017.

* cited by examiner

CLOSED IV ACCESS DEVICE WITH PADDLE GRIP NEEDLE HUB AND FLASH CHAMBER

RELATED APPLICATIONS

This application is a continuation of U.S. patent application Ser. No. 16/833,058, filed Mar. 27, 2020, and entitled CLOSED IV ACCESS DEVICE WITH PADDLE GRIP NEEDLE HUB AND FLASH CHAMBER, which is a continuation of U.S. patent application Ser. No. 15/286,188, filed Oct. 5, 2016, and entitled CLOSED IV ACCESS DEVICE WITH PADDLE GRIP NEEDLE HUB AND FLASH CHAMBER, which claims the benefit of U.S. Provisional Patent Application No. 62/247,617, which was filed on Oct. 28, 2015, U.S. Provisional Patent Application No. 62/247,596, which was filed on Oct. 28, 2015, U.S. Provisional Patent Application No. 62/296,383, which was filed on Feb. 17, 2016, U.S. Provisional Patent Application No. 62/247,599, which was filed Oct. 28, 2015, U.S. Provisional Patent Application Ser. No. 62/247,607, which was filed Oct. 28, 2015, U.S. Provisional Patent Application Ser. No. 62/247,621, which was filed Oct. 28, 2015, U.S. Provisional Patent Application Ser. No. 62/247,624, which was filed Oct. 28, 2015, U.S. Provisional Application No. 62/247,626, which was filed on Oct. 28, 2015, and U.S. Provisional Application No. 62/296,385, which was filed on Feb. 17, 2016, each of which is incorporated herein by reference in their entirety.

BACKGROUND

When an IV access device is identified as being "closed" or "integrated," it generally refers to the fact that the device is configured to prevent blood from escaping the device during insertion of the catheter. Typically, such IV access devices accomplish this by integrating an extension set with the catheter adapter.

FIG. 1 illustrates an example of a prior art closed IV access device 100. Device 100 includes a catheter adapter 101 from which a catheter 101*a* extends, a needle hub 102 from which a needle 102*a* extends, an extension tube 103 that is coupled to catheter adapter 101 at one end and includes a Y-adapter 104 coupled to the other end, and a clamp 107 for blocking or limiting fluid flow through extension tube 103. Y-adapter 104 includes a port 105 and a vent plug 106. Device 100 can be a closed system by incorporating fluid flow blocking components (e.g., a septum or vent) into each external opening of the device such as into a proximal end of catheter adapter 101 and into any ports in adapter 104.

To facilitate proper insertion of the needle in a closed system, it is typical for the needle to include a flashback notch towards its distal end. This flashback notch is oftentimes positioned within the catheter so that blood flowing out through the flashback notch will be visible within the catheter. When blood is seen flowing through the flashback notch, the clinician can know that the needle tip is contained within a vein. However, a flashback notch alone may not be sufficient to provide confirmation of proper catheter placement. For example, even if the needle tip is contained within the vein, the tip of the catheter may not be. Also, during needle withdrawal, it is possible that the catheter tip may be displaced from within the vein.

For these reasons, closed IV access devices oftentimes are configured to allow blood to flow into the extension tube to provide a secondary confirmation of proper catheter placement. For example, access device 100 may include a vent plug that is coupled to a port of luer adapter 104. The vent plug can allow air to escape from extension tube 103 thereby allowing the patient's blood pressure to cause blood to flow into extension tube 103. If blood flows into extension tube 103, the clinician can know that the tip of catheter 101*a* is properly positioned within the patient's vein.

Although using the extension tube of a closed system is an effective way of providing secondary confirmation of proper catheter placement, some catheter insertion techniques prevent it from being used. For example, it is common in some countries to prime extension tube 103 with saline solution prior to inserting catheter 101*a*. In such cases, because extension tube 103 will be filled with saline during catheter insertion, blood will not flow into extension tube 103 to provide the secondary confirmation.

BRIEF SUMMARY OF THE INVENTION

The present invention is generally directed to a closed IV access device that is configured to provide secondary confirmation of proper catheter placement without requiring blood to flow into the extension tube. Although a closed IV access device in accordance with the present invention can be of primary benefit in instances where the extension tube is pre-primed with saline solution, the present invention may also be employed when the extension tube is not primed.

An IV access device can include a needle hub that incorporates a flash chamber. The flash chamber can be used to provide visual confirmation of proper catheter placement within a vein. The flash chamber can include a path-defining structure to facilitate identifying whether blood is continually flowing into the flash chamber. The flash chamber may also be removable from the needle hub. In some cases, the needle hub may include a paddle grip that facilitates insertion of the catheter and separation of the needle hub from the catheter adapter.

In one embodiment, the present invention is implemented as an IV access device that includes a catheter adapter from which a catheter extends distally; an extension tube coupled to the catheter adapter; and a needle hub from which a needle extends distally. The needle hub is coupled to the catheter adapter such that the needle extends through the catheter. The needle hub further includes a flash chamber that is in fluid communication with a lumen of the needle thereby allowing blood to flow into the flash chamber when a distal tip of the needle is contained within a patient's vein.

In another embodiment, the present invention is implemented as an IV access device that includes a catheter adapter from which a catheter extends distally; an extension tube coupled to the catheter adapter; and a needle hub from which a needle extends distally. The needle hub is coupled to the catheter adapter such that the needle extends through the catheter. The needle hub includes a flash chamber, a proximal end of the needle forming a fluid pathway for blood to flow into the flash chamber. The flash chamber includes a plug that vents air but blocks the flow of blood thereby allowing blood to flow into the flash chamber when a distal tip of the needle is contained within a patient's vein.

In another embodiment, the present invention is implemented as an IV access device comprising a catheter adapter having a wing and a catheter that extends distally; an extension tube that is coupled to the catheter adapter; and a needle hub that includes a paddle grip, a needle that extends through the catheter when the needle hub is coupled to the catheter adapter, and a flash chamber. A proximal end of the needle provides a fluid pathway for blood to flow into the flash chamber when a distal tip of the needle is contained within a patient's vein.

These and other features and advantages of the present invention may be incorporated into certain embodiments of the invention and will become more fully apparent from the following description and appended claims, or may be learned by the practice of the invention as set forth hereinafter. The present invention does not require that all the advantageous features and all the advantages described herein be incorporated into every embodiment of the invention.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof that are illustrated in the appended drawings. These drawings depict only typical embodiments of the invention and are not therefore to be considered to limit the scope of the invention.

DETAILED DESCRIPTION OF THE INVENTION

Figure 1:
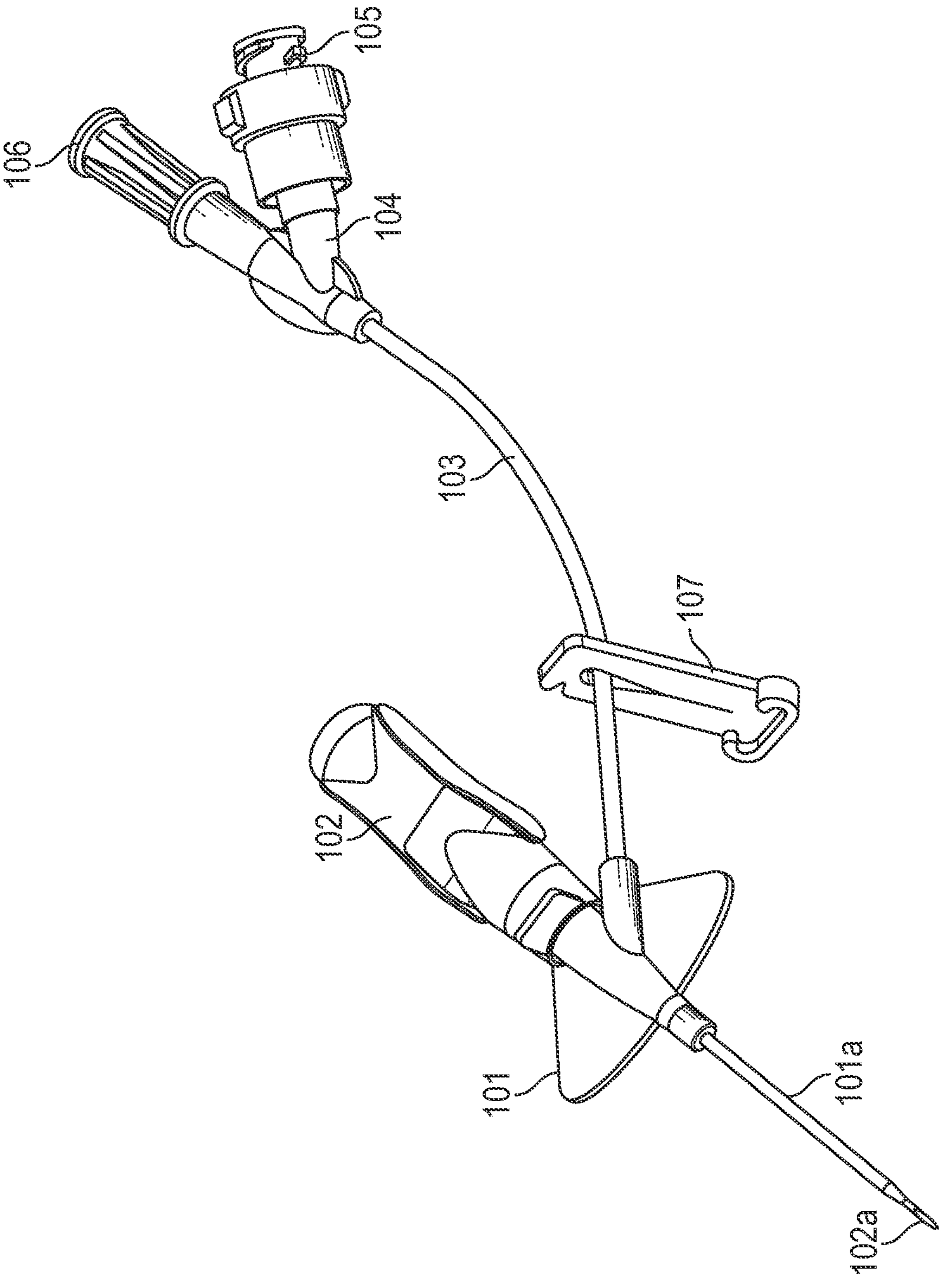
FIG. 1 illustrates a prior art closed IV access device.
Figure 2:
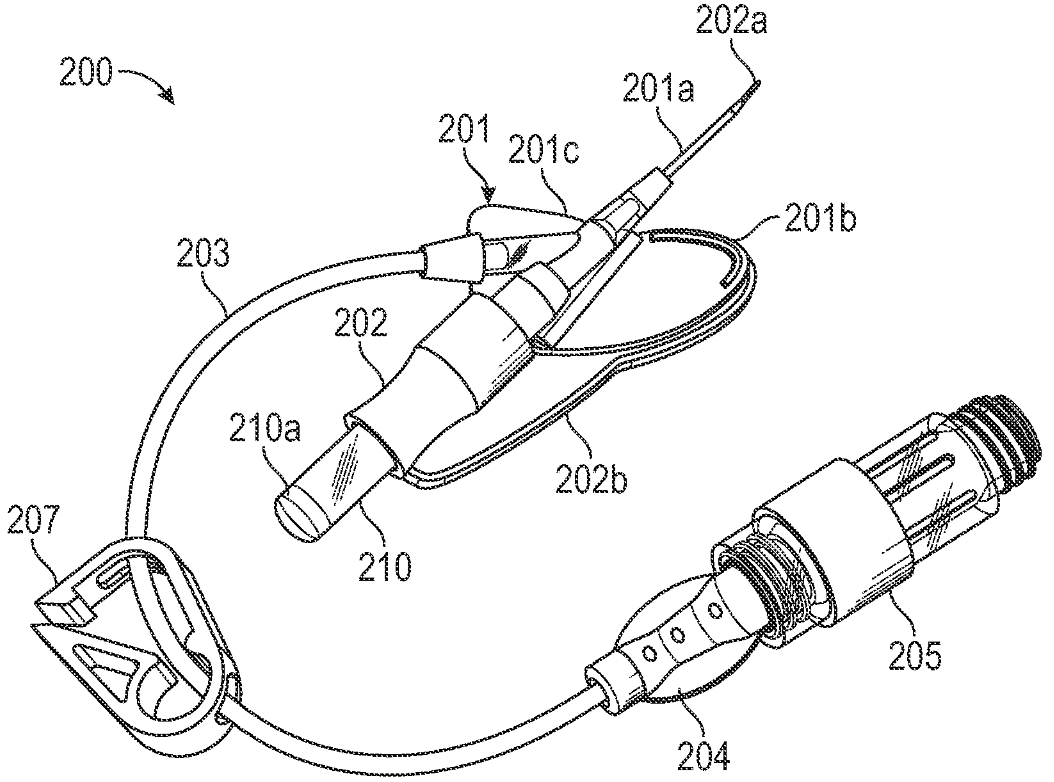
FIG. 2 illustrates a closed IV access device in accordance with one or more embodiments of the present invention.

FIG. 2 illustrates an example of a closed IV access device 200 that is configured in accordance with one or more embodiments of the present invention. Access device 200 includes a catheter adapter 201 from which a catheter 201*a* extends distally, a needle hub 202 from which a needle 202*a* extends distally, an extension tube 203 that is fluidly coupled to a lumen of catheter adapter 201, and a clamp 207 for restricting the flow of fluid through extension tube 203. A luer adapter 204 or other type of adapter can be coupled to the end of extension tube 203. Also, a luer access device 205, such as one that includes a septum, may be coupled to luer adapter 204.

Catheter adapter 201 can include a stabilization platform formed by wings 201*b* and 201*c* which extend outwardly from opposite sides of catheter adapter 201. As shown in FIG. 2, access device 200 is configured for right-hand use in that extension tube 203 couples to the left side of catheter adapter 201 such that wing 201*b* is fully exposed. This can facilitate gripping wing 201*b* with the thumb of the right hand. In some embodiments, an interface for coupling extension tube 203 to catheter adapter 201 can be formed into wing 201*c*. Of course, in an access device designed for left-hand use, wings 201*b*, 201*c* and extension tube 203 would be on opposite sides of catheter adapter 201 from what is shown in FIG. 2.

Needle hub 202 includes a paddle grip 202*b* that extends outwardly from the right side of needle hub 202 and has a shape that generally corresponds to the shape of wing 201*b*. Accordingly, paddle grip 202*b* can be positioned directly beneath wing 201*b* so that wing 201*b* and paddle grip 202*b* can be sandwiched between the clinician's thumb and index finger during insertion of catheter 201*a*. By configuring paddle grip 202*b* in this manner, the clinician can easily withdraw needle hub 202 from catheter adapter 201 by simply sliding the index finger backwards with respect to the thumb thereby causing the paddle grip 202*b* to slide backward away from wing 201*b*.

Figure 3:
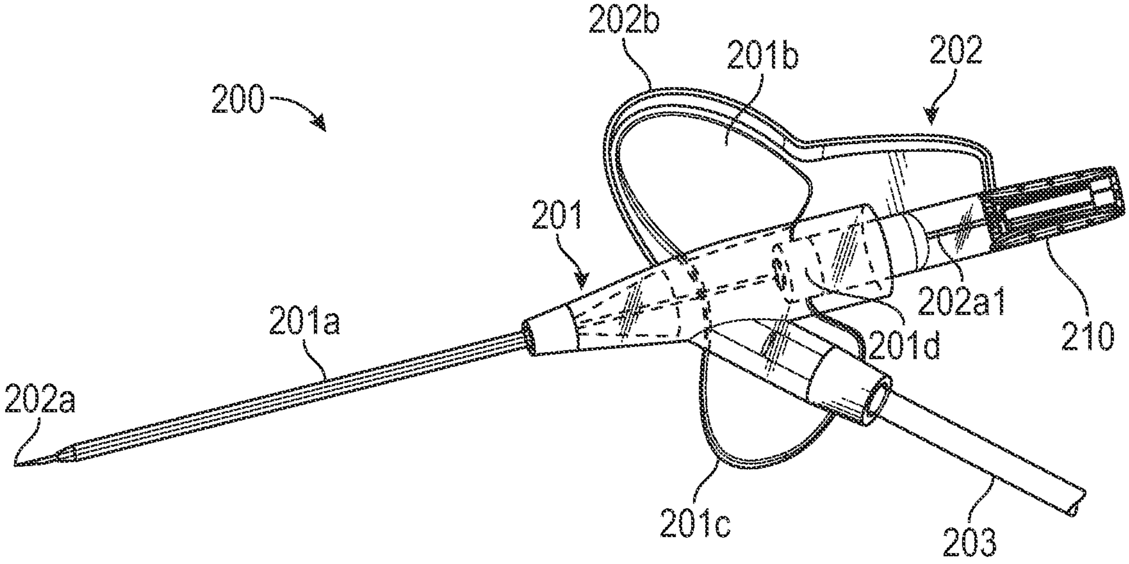
FIG. 3 also illustrates a closed IV access device in accordance with one or more embodiments of the present invention.

Needle hub 202 also includes a flash chamber 210 that is coupled to the proximal end of needle hub 202. As is better shown in FIG. 3, flash chamber 210 can include a porous vent plug 210*a* that allows air to escape through a proximal opening in needle hub 202 while preventing blood from escaping. Alternatively, flash chamber 210 could include different means for venting air but blocking blood including, e.g., a membrane, filter paper, woven or non-woven material, a plug that includes venting channels along an interface between the proximal end of needle hub 202 and the plug, etc. Also, a proximal end of needle 202*a* can extend into flash chamber 210 and can include an opening 202*a*1to allow blood to flow out of needle 202*a* and into flash chamber 210.

Needle 202*a* can include a notch (not shown) towards its distal end for providing flashback. The flashback provided through this notch can provide a primary confirmation that catheter 201*a* has been properly placed within a vein. Additionally, flash chamber 210 can provide secondary confirmation that catheter 201*a* is properly positioned within the vein. In particular, because the proximal end of needle 202*a* opens into flash chamber 210 and because flash chamber is vented to the external environment via plug 210*a*, when the distal end of needle 202*a* is properly positioned within a vein, the patient's blood pressure will cause blood to flow into flash chamber 210. Because this flow of blood into flashback chamber 210 is accomplished via needle 202*a*, this secondary confirmation can be obtained even if extension tube 203 is primed with saline prior to insertion of catheter 201*a*.

Once the clinician has determined that catheter 201*a* has been properly placed, needle hub 202 can be withdrawn from catheter adapter 201 by simply sliding paddle grip 202*b* backwards away from wing 201*b*. Catheter adapter 201 can include a septum 201*d* through which needle 202*a* can extend. Septum 201*d* can reseal after withdrawal of needle 202*a* to prevent any fluid from escaping out through the proximal opening of catheter adapter 201.

Figure 4:
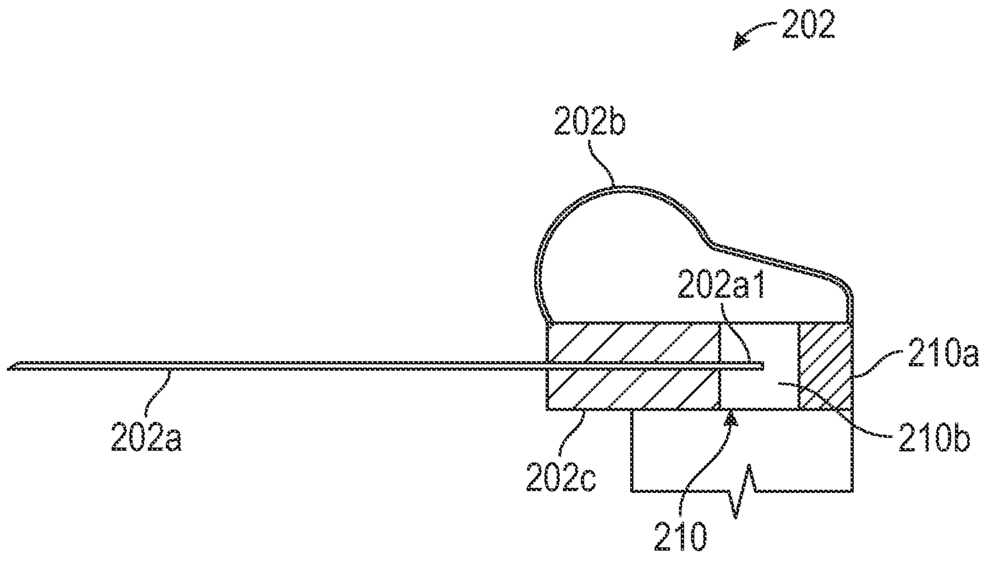
FIG. 4 illustrates a cross-sectional view of an example needle hub that includes a flash chamber in accordance with one or more embodiments of the present invention.

FIG. 4 provides a cross-sectional view of one embodiment of needle hub 202. As shown, needle hub 202 can include a needle retaining portion 202*c* through which needle 202*a* extends. Needle retaining portion 202*c* can be configured to secure needle 202*a* to needle hub 202 in any suitable manner such as via an adhesive or a friction fit. In some embodiments, needle retaining portion 202*c* can be configured to insert within a proximal opening of catheter adapter 201 to secure needle hub 202 to catheter adapter 201.

Flash chamber 210 generally comprises plug 210*a* and a chamber 210*b*. Opening 202*a*1of needle 202*a* can be positioned within chamber 210*b* so that blood may flow into and accumulate within chamber 210*b*. Plug 210*a* can be positioned between chamber 210*b* and the external environment to allow air to be vented from chamber 210*b* as blood flows towards and into chamber 210*b*.

In some embodiments, the dimension of a lumen of needle 202*a* may be configured to cause blood to flow into chamber 210*b* at a particular rate. For example, it may be desirable to limit the flow of blood into chamber 210*b* so that chamber 210*b* will not become full until catheter 201*a* has been positioned within a vein for a specified amount of time. In some cases, this specified amount of time may be as long as 20 seconds. Accordingly, one or more dimensions of the fluid pathway through needle 202*a* can be configured to provide a desired flowrate. Alternatively or additionally, plug 210*a* may be configured to vent air at a specified rate to limit the flowrate of blood into chamber 210*b*.

In some cases, however, it may be difficult for the clinician to determine whether blood is continually flowing into chamber 210*b*. For example, if catheter 201*a* were initially placed within the vein thereby causing blood to flow into chamber 210*b*, but was then positioned outside the vein, it may be difficult for the clinician to determine that blood is no longer flowing into chamber 210*b*. This may be especially true when needle 202*a* is configured to provide a slow flowrate into chamber 210*b*. To address this issue, flash chamber 210 can be configured to include a path-defining structure.

Figure 5:
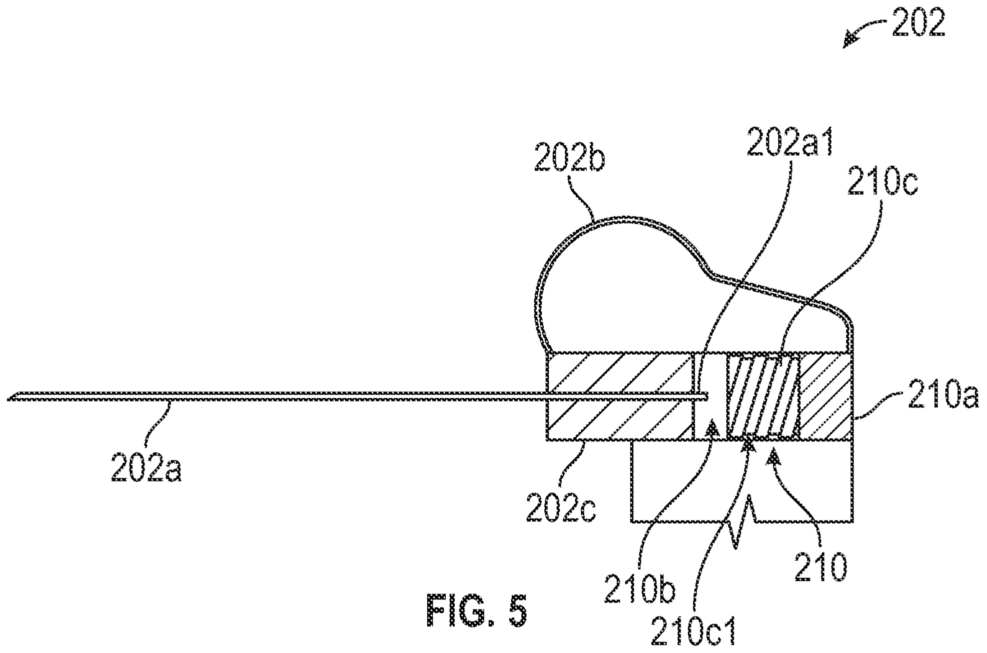
FIG. 5 illustrates a cross-sectional view of an example needle hub that includes a flash chamber having a path-defining structure in accordance with one or more embodiments of the present invention.

FIG. 5 illustrates an example of a path-defining structure 210*c* that can be incorporated into flash chamber 210. It is noted that FIG. 5 depicts a cross-sectional view of needle hub 202 with path-defining structure 210*c* not being shown as a cross-section so that the outer surface of the path-defining structure can be seen. As in FIG. 4, flash chamber 210 includes a chamber 210*b* in which opening 202*a*1 of needle 202*a* is contained. Path-defining structure 210*c* is positioned between plug 210*a* and opening 202*a*1 and includes a pathway 210*c*1 through which blood can flow. In particular, pathway 210*c*1 extends around the outer surface of path-defining structure 210*c*. The outer diameter of path-defining structure 210*c* can be substantially the same as the inside diameter of flash chamber 210 such that blood is confined to flowing through pathway 210*c*1 to reach plug 210*a*.

Pathway 210*c*1 can function to increase the distance that blood can flow within flash chamber 210. Because pathway 210*c*1 can have smaller cross-sectional dimensions than chamber 210*b*, it will be easier to detect the flow of blood into flash chamber 210. In particular, by including path-defining structure 210*c*, the clinician will be able to easily see the blood advance along pathway 210*c*1 towards plug 210*a*. As long as the blood continues to advance along pathway 210*c*1, the clinician can know that catheter 201*a* is likely positioned correctly.

In this example, pathway 210*c*1 is shown as having a spiral shape; however, path-defining structure 210*c* can include any suitably-shaped pathway. Also, although FIG. 5 illustrates that flash chamber 210 includes a chamber 210*b* that is separate from pathway 210*c*1 (i.e., that path-defining structure 210*c* is spaced from needle retaining portion 202*c*), in some embodiments, path-defining structure 210*c* may be configured such that pathway 210*c*1 extends overtop the proximal end of needle 202*a* so that blood flows directly into pathway 210*c*1 rather than flowing first into chamber 210*b*.

Further, in some embodiments, path-defining structure 210*c* and needle retaining portion 202*c* can be the same structural component. However, using a separately-formed path-defining structure 210*c* may be preferred in many cases since it facilitates the manufacture of needle hub 202. For example, needle hub 202 could be molded with a proximal opening into which a separately formed path-defining structure 210*c* and plug 210*a* could be inserted.

Figure 6:
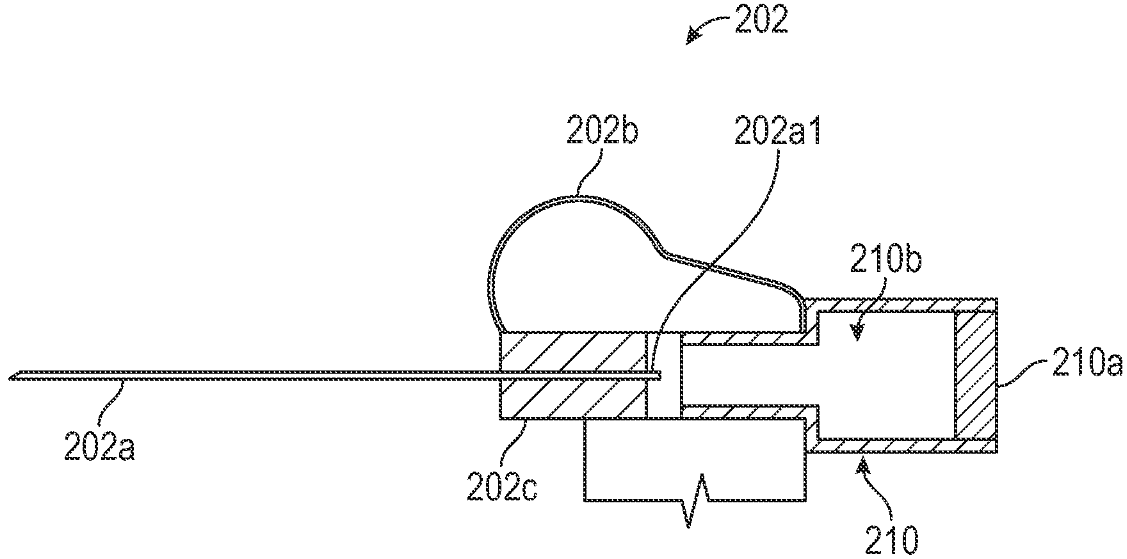
FIG. 6 illustrates a cross-sectional view of an example needle hub that includes a flash chamber that is removable in accordance with one or more embodiments of the present invention.
Figure 7:
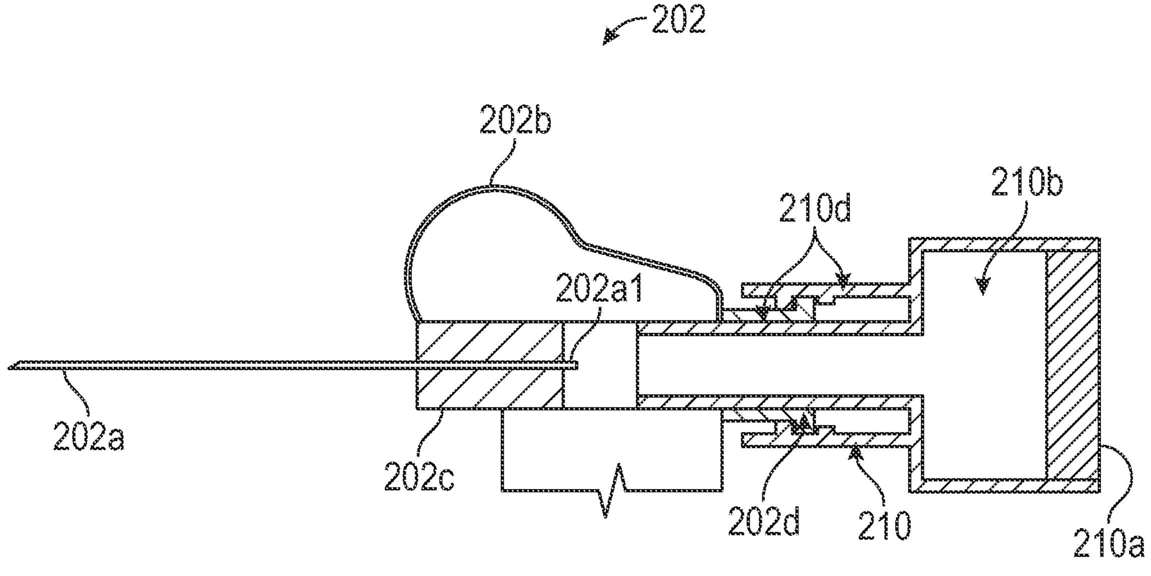
FIG. 7 illustrates a cross-sectional view of an example needle hub that includes a flash chamber that is removable in accordance with one or more embodiments of the present invention.

In some embodiments, flash chamber 210 can be configured to be removable from needle hub 202. FIGS. 6 and 7 each illustrate examples of how this can be accomplished. In FIG. 6, and as described above, flash chamber 210 forms chamber 210*b* and contains plug 210*a*. Additionally, flash chamber 210 is configured with a distal end that removably inserts into a proximal opening of needle hub 202. In this configuration, after chamber 210*b* has been filled with blood and needle hub 202 has been separated from catheter adapter 201, flash chamber 210 can be pulled out from needle hub 202. A distal opening of flash chamber 210 can be configured to prevent the blood from escaping chamber 210*b* until a desired time. For example, the size of the distal opening of flash chamber 210 can be sufficiently small to prevent the blood from escaping until the body of flash chamber 210 is squeezed. In this way, flash chamber 210 could be employed to perform point-of-care testing on the blood.

In FIG. 7, flash chamber 210 is also configured to be removable. However, in contrast to FIG. 6, needle hub 202 includes a female luer port 202*d* and flash chamber 210 includes a male luer lock coupling 210*d* to allow flash chamber 210 to be coupled to port 202*d*. Coupling 210*d* could alternatively be configured as a male luer slip coupling. Flash chamber 210 could be used in a similar manner as described above with respect to FIG. 6. Additionally, because needle hub 202 includes a female luer port 202*d*, prior to removing needle hub 202 from catheter adapter 201, flash chamber 210 could be removed to allow a separate device, such as a blood collection holder, to be connected to female luer port 202*d* to collect larger blood samples.

Figure 8A:
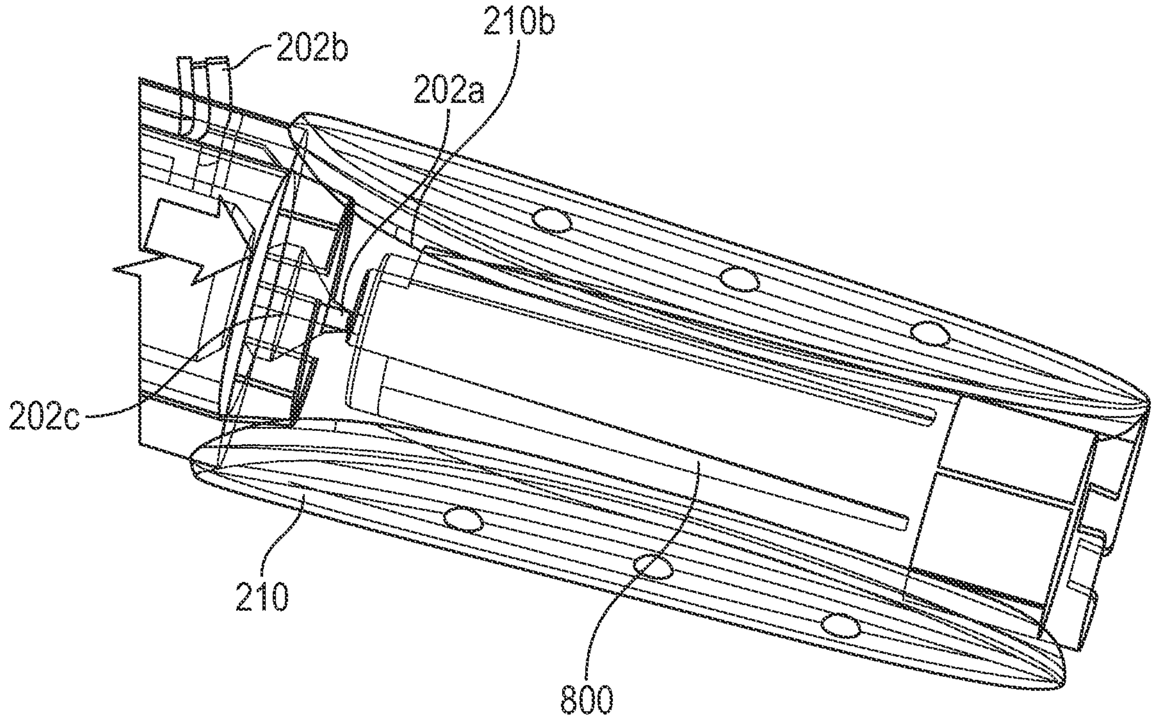
FIG. 8A illustrates another embodiment of a flash chamber that includes a path-defining structure.
Figure 8B:
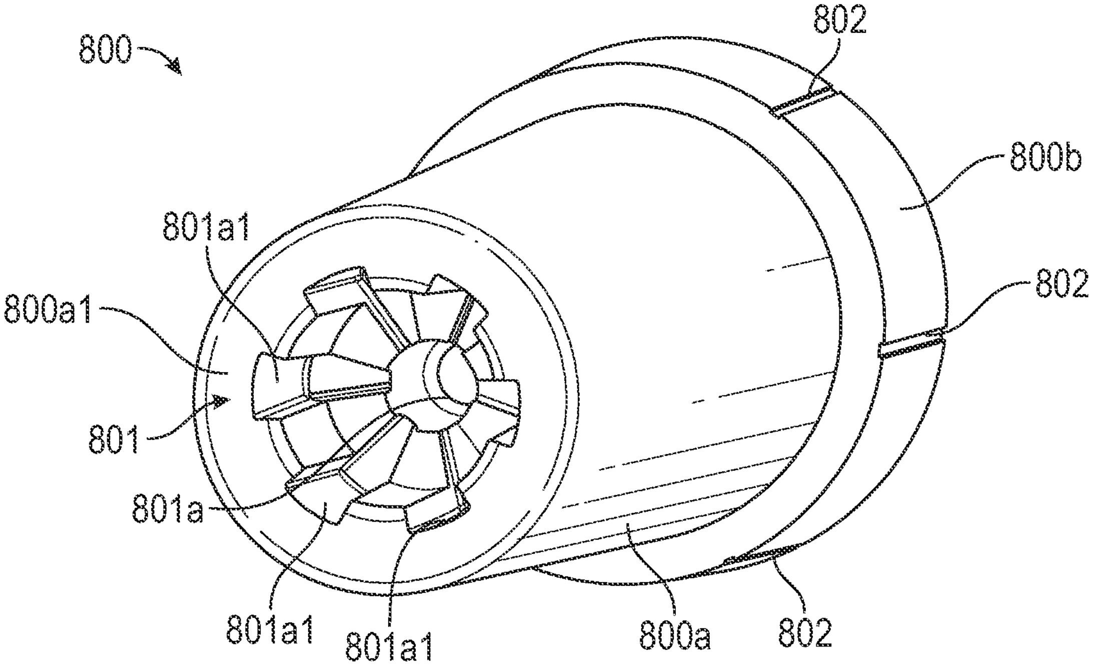
FIG. 8B illustrates the path-defining structure of FIG. 8A in isolation.

FIG. 8A illustrates an embodiment of flash chamber 210 that includes a path-defining structure 800 while FIG. 8B illustrates path-defining structure 800 in isolation. As with path-defining structure 210*c*, path-defining structure 800 can be positioned within chamber 210*b* in such a way as to facilitate visualizing the flow of blood into chamber 210*b*.

Path-defining structure 800 includes a distal portion 800*a* and a proximal portion 800*b*. In some embodiments, proximal portion 800*b* can have an outer dimension that substantially matches an inner dimension of a proximal end of chamber 210*b* such that a fluid-tight seal is formed between the two components. Proximal portion 800*b* can include venting grooves 802 which are sized to allow air, but not fluid, to escape from chamber 210*b*. In other words, proximal portion 800*b* can function as a vent plug.

Distal portion 800*a* can have a reduced outer dimension compared to the outer dimension of proximal portion 800*b*. The inner dimension of chamber 210*b* with respect to the outer dimension of distal portion 800*a* can also be configured such that a spacing or channel will exist between distal portion 800*a* and the inner wall of chamber 210*b* only along the top of flash chamber 210. For example, as is better shown in FIG. 8C, with path-defining structure 800 inserted into chamber 210*b*, a channel will exist above path-defining structure 800. However, around the remaining portions of path-defining structure 800, the outer surface of distal portion 800*a* can contact the inner wall of chamber 210*b*. In this way, blood/fluid will only be allowed to flow along the outer surface of distal portion 800*a* within the channel. Since this channel is formed along the top of flash chamber 210, which will be oriented towards the clinician during insertion, the clinician will be able to visualize the rate of blood flow.

To allow blood to flow from the proximal end of needle 202*a* into this channel, an opening 801 can be formed in a distal end 800*a*1 of distal portion 800*a* as is best shown in FIG. 8B. Opening 801 can include a central portion 801*a* that extends further into distal portion 800*a* then the remainder of opening 801. The proximal end (or at least a proximal opening) of needle 202*a* can be positioned within this central portion 801*a*. A number of leaking channels 801*a*1 can be symmetrically spaced around an inner surface of opening 801 and can extend from distal end 800*a*1 to central portion 801*a*. Any of leaking channels 801*a*1 can serve as a fluid pathway by which blood escaping the proximal end of needle 202*a* can flow from central portion 801*a* towards the channel formed above path-defining structure 800.

Figure 8C:
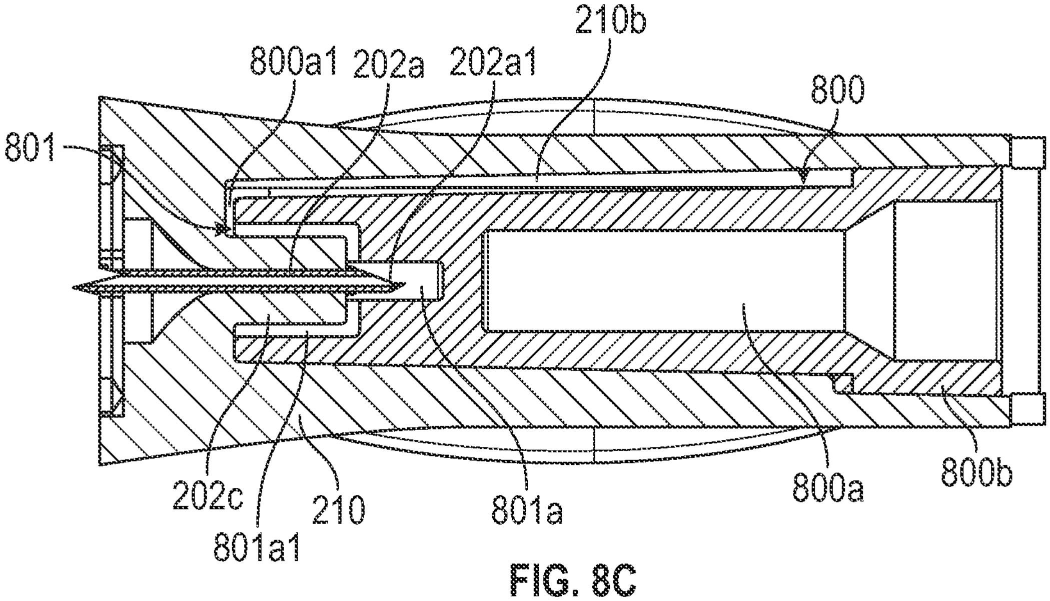
FIG. 8C illustrates a cross-sectional view of the flash chamber of FIG. 8A.
Figure 8D:
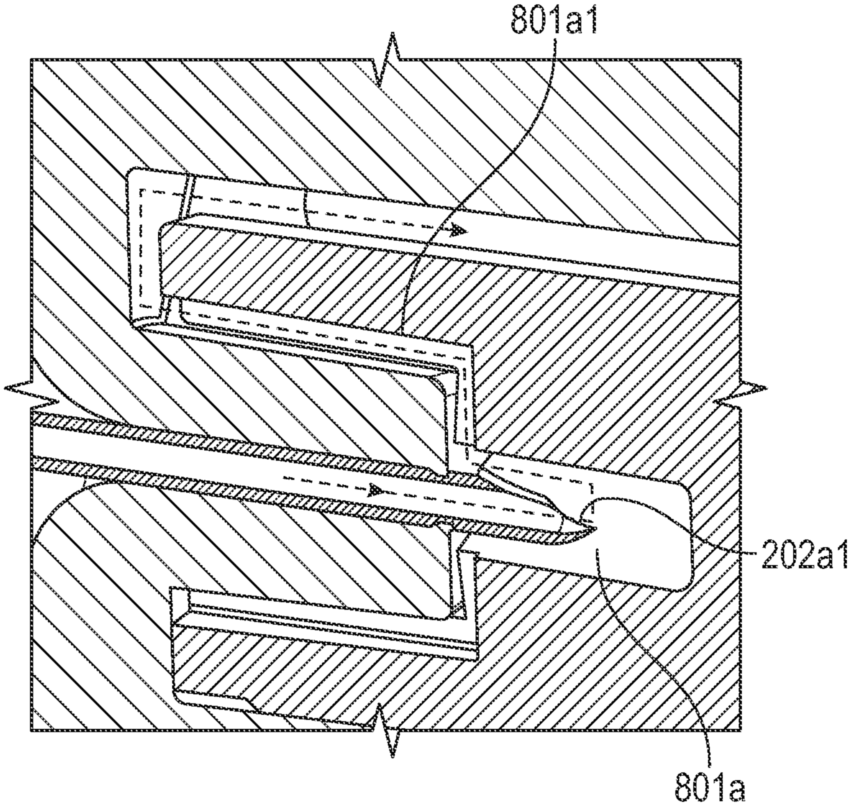
FIG. 8D illustrates another cross-sectional view of the flash chamber of FIG. 8A in which the direction of blood flow is identified.

Leaking channels 801*a*1 can be symmetrically spaced around opening 801 to thereby allow path-defining structure 800 to be inserted into chamber 210*b* in any orientation. In other words, regardless of the orientation of path-defining structure 800, at least one leaking channel 801*a*1 will be positioned in an upward orientation and will intersect with the channel to thereby provide a pathway to the channel. As shown in FIG. 8C, the inner surface of chamber 210*b* can be shaped such that the channel will wrap around distal end 800*a*1 at the top of chamber 210*b* (i.e., a gap will exist between a top portion of distal end 800*a*1 and the inner surface of chamber 210*b*). Accordingly, as represented by the arrow in FIG. 8D, blood can flow out of needle 202*a* via opening 202*a*1 and into central portion 801*a*. Then, although the blood may flow into each of leaking channels 801*a*1, a fluid pathway will only be provided between the leaking channel that is oriented upward due to distal end 800*a*1 contacting the inner wall of chamber 210*b* where the other leaking channels are positioned. Therefore, as the blood fills central portion 801*a* and leaking channels 801*a*1, it will ultimately flow around the top portion of distal end 800*a*1 and then proximally within the channel.

Figure 8E:
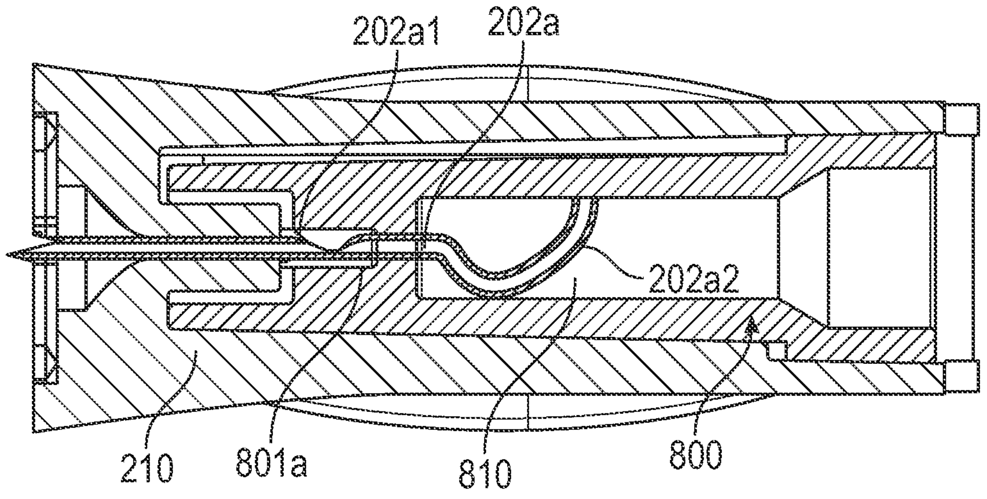
FIG. 8E illustrates an embodiment of the flash chamber of FIG. 8A in which a proximal end of the needle extends into and is secured within the path-defining structure.

To secure needle 202*a* and to ensure that opening 202*a*1 remains positioned within central portion 801*a*, various techniques can be employed. For example, in FIG. 8E, needle 202*a* is shown as having a proximal portion 202*a*2 that extends proximally beyond opening 202*a*1 and through a proximal wall of central portion 801*a*. In this embodiment, path-defining structure 800 includes a proximal chamber 810 opposite central portion 801*a* within which proximal portion 202*a*2 of needle 202*a* is positioned. Proximal portion 202*a*2 can be curled or otherwise altered to prevent it from being pulled distally through the passageway between central portion 801*a* and proximal chamber 810. Also, in some embodiments, adhesive potting may be deposited within proximal chamber 810 around proximal portion 202*a*2 to further secure proximal portion 202*a*2. In such embodiments, the adhesive potting may additionally seal the passageway to prevent blood from flowing into proximal chamber 810. Alternatively, the passageway may be sized such that proximal portion 202*a*2 alone blocks fluid flow into proximal chamber 810.

Figure 8F:
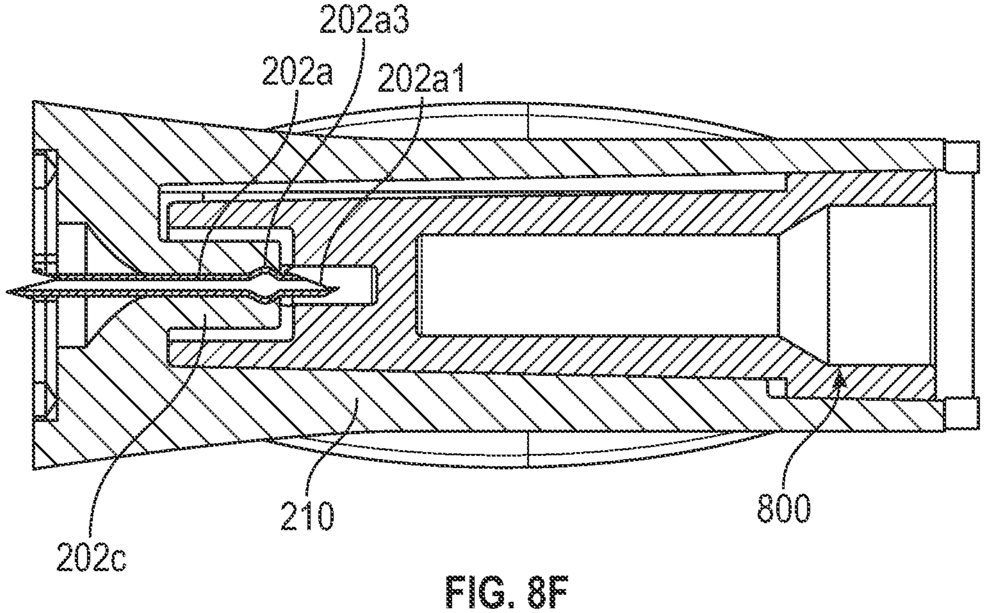
FIG. 8F illustrates an embodiment of the flash chamber of FIG. 8A in which the needle includes a bulge for securing the needle to the flash chamber.

FIG. 8F illustrates an alternate embodiment for securing needle 202*a* in position. As shown, needle 202*a* may include a bumped area 202*a*3 (which may integrally molded, separately formed and coupled to needle 202*a* with an adhesive, or otherwise formed) that has an outer dimension sufficient to prevent needle 202*a* from being pulled through needle retaining portion 202*c*. Bumped area 202*a*3 can be positioned relative to opening 202*a*1 so that opening 202*a*1 remains positioned within central portion 801*a*. In some embodiments, needle retaining portion 202*c* may include a recessed section into which bumped area 202*a*3 can be positioned to further prevent area 202*a* from moving in a proximal or distal direction.

Figure 8G:
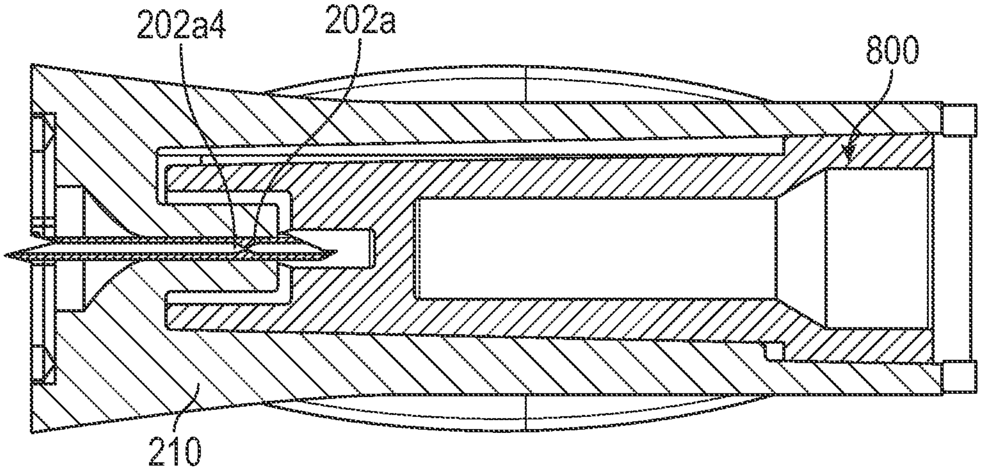
FIG. 8G illustrates an embodiment of the flash chamber of FIG. 8G in which the needle includes a crimp to slow the rate of blood flow into the flash chamber.

In some embodiments, needle 202*a* may be modified to reduce the rate at which blood will flow through the needle. For example, in FIG. 8G, needle 202*a* is shown as having a crimp 202*a*4 towards its proximal end. Crimp 202*a*4 reduces the inside dimension of needle 202*a* thereby slowing the rate at which blood will flow into central portion 801*a*. Reducing the rate of blood flow into central portion 801*a* will likewise reduce the rate of blood flow along the channel formed above path-defining structure 800 thereby facilitating identifying when needle 202*a* has been properly positioned within the patient.

Figure 9A:
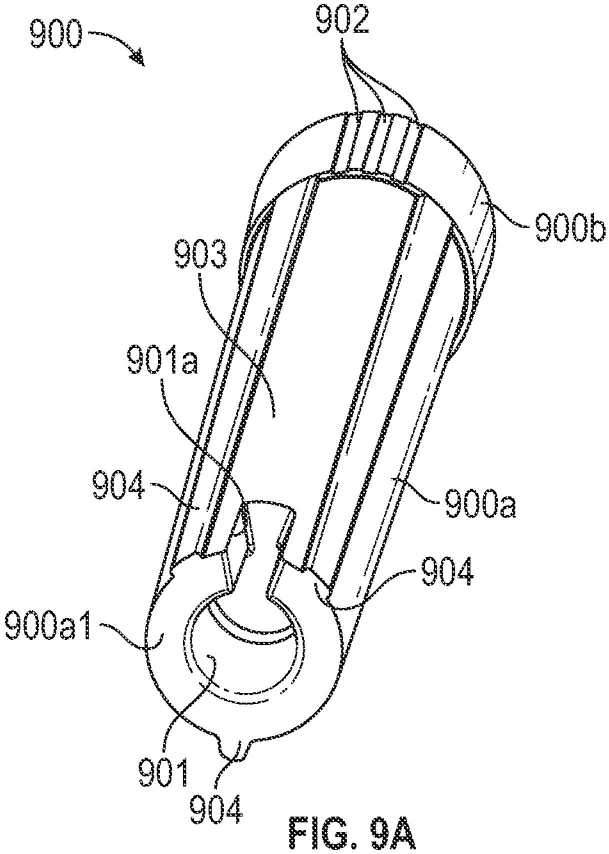
FIGS. 9A and 9B illustrate different views of an alternate embodiment of a path-defining structure that can be employed within a flash chamber.
Figure 9B:
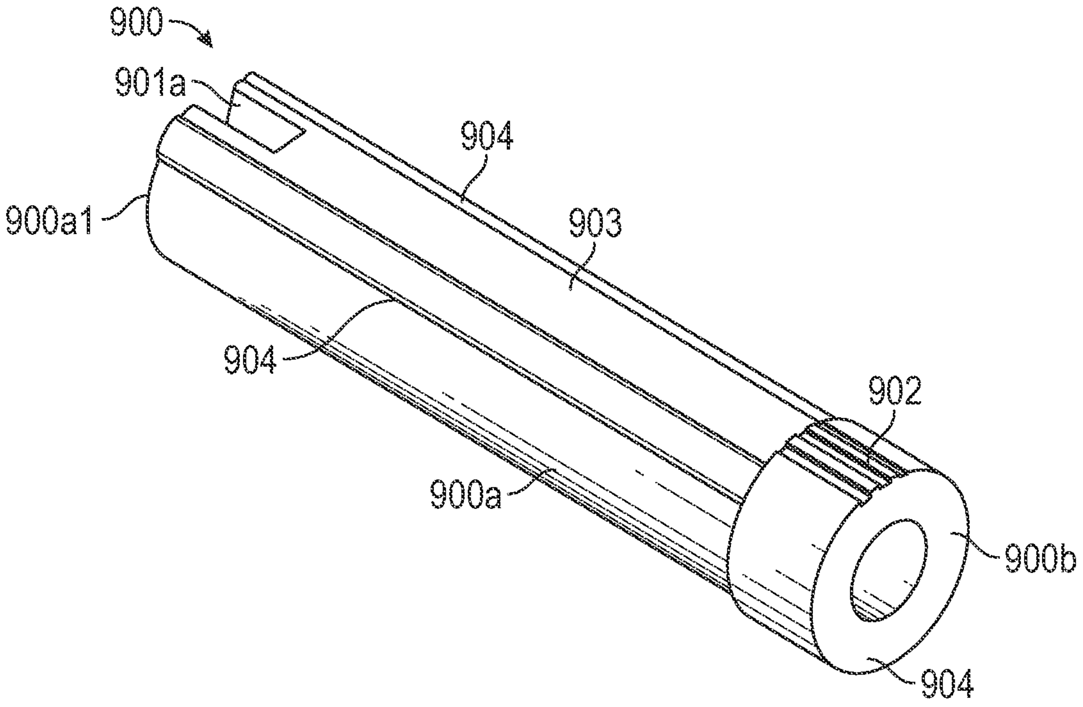

FIGS. 9A and 9B illustrate another embodiment of a path-defining structure 900 that can function in a similar manner as path-defining structure 800. In particular, path-defining structure 900 can be configured to cause blood to flow along a visualization channel formed at the top of flash chamber 210.

Path-defining structure 900 can include a distal portion 900*a* and a proximal portion 900*b*. Proximal portion 900*b* can include venting grooves 902 that function to vent air from a proximal end of flash chamber 210. Unlike distal portion 800*a* of path-defining structure 800 which can be inserted into chamber 210*b* in any orientation, distal portion 900*a* can include a visualization channel 903 and various alignment ribs 904 that are configured for a particular orientation. The inner surface of chamber 210*b* can be configured to accommodate alignment ribs 904 in such a manner that path-defining structure 900 will be oriented with visualization channel 903 facing upwards. For example, chamber 210*b* could include lengthwise grooves or tabs which interface with alignment ribs 904 to require insertion of path-defining structure 900 in the correct orientation and to prevent rotation. Alternatively, chamber 210*b* could be configured to form a frictional fit with path-defining structure 900 which would prevent its rotation once inserted into the chamber. In such cases, alignment ribs 904 would not be required.

Figure 9C:
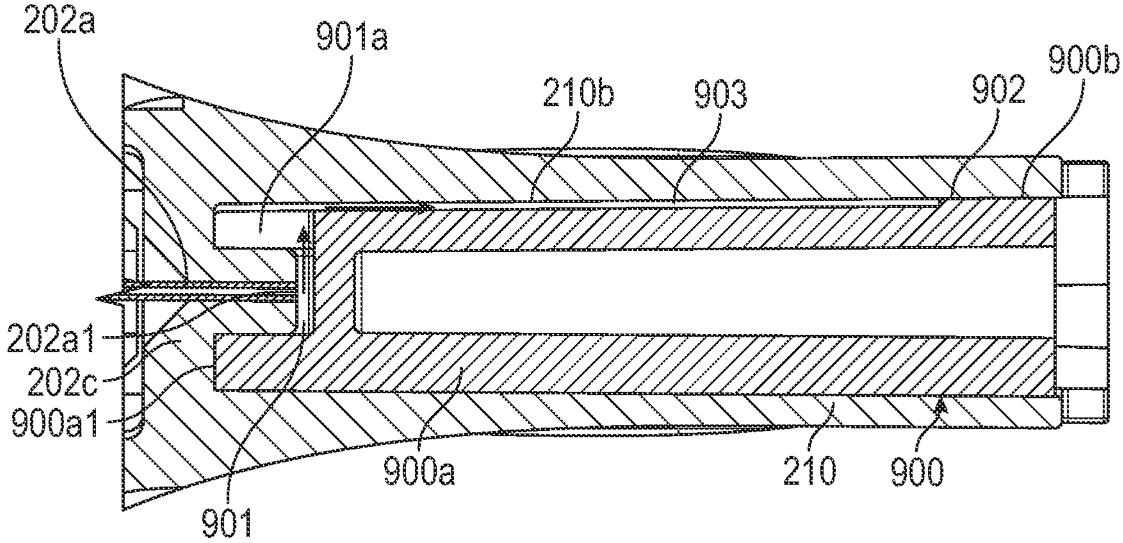
FIG. 9C illustrates a cross-sectional view of a flash chamber that includes the path-defining structure of FIGS. 9A and 9B.

Distal portion 900*a* of path-defining structure 900 can include a distal end 900*a*1 having an opening 901. A leaking channel 901*a* can extend between opening 901 and visualization channel 903. In a similar manner as described above, blood can flow out of opening 202*a*1 into opening 901 through leaking channel 901*a* and into visualization channel 903 as represented by the arrows in FIG. 9C. Although not depicted in this embodiment, the various configurations of needle 202*a* shown in FIGS. 8E-8G can also be employed in conjunction with path-defining structure 900.

Figure 10:
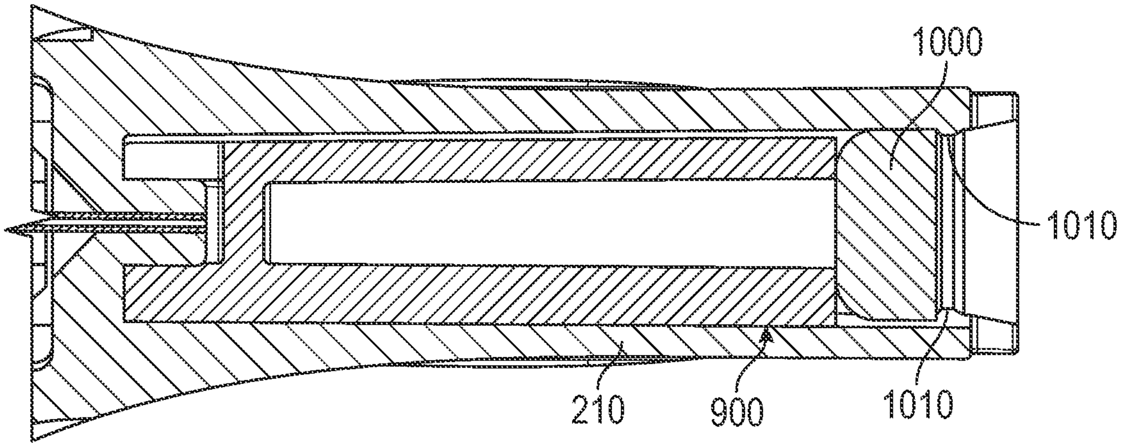
FIG. 10 illustrates an embodiment of a flash chamber that includes a path-defining structure and a vent plug that secures the path-defining structure within the flash chamber.

FIG. 10 illustrates an embodiment of a flash chamber 210 in which a vent plug 1000 is employed in place of distal portion 900*b*. Also, although not shown, vent plug 1000 could equally be employed in place of distal portion 800*b*. As depicted in FIG. 10, vent plug 1000 is separate from and positioned proximally to path-defining structure 900. Vent plug 1000 can primarily function to vent air but block fluid. However, in some embodiments, vent plug 1000 may also be configured to secure path-defining structure 800/900 in place. For example, flash chamber 210 can include protrusion(s) 1010 that are positioned proximally to vent plug 1000 when vent plug 1000 is inserted into chamber 210*b*. Protrusions 1010 can prevent vent plug 1000, and therefore path-defining structure 800/900, from moving proximally within chamber 210*b*. In some embodiments, a single protrusion 1010 may extend fully around the entire inner circumference of flash chamber 210, while in other embodiments, multiple protrusions 1010 may be spaced around the inner circumference. Also, in some embodiments, protrusion 1010 may extend fully around the inner circumference (thereby forming an inner ring) and can be positioned such that it extends into vent plug 1000 (e.g., shifted to the left form what is shown in FIG. 10). In these embodiments, protrusion 1010 can not only function to retain vent plug 1000 within chamber 210*b* but can also form a seal around vent plug 1000.

Figure 11A:
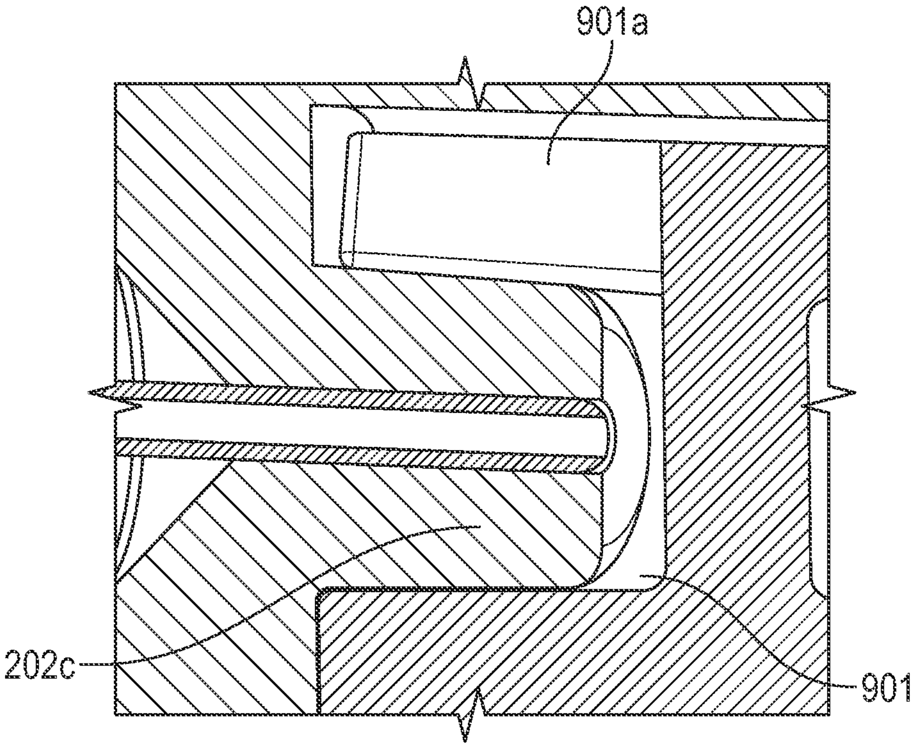
FIGS. 11A-11C each illustrate an example of how a path-defining structure can be secured within a flash chamber.
Figure 11B:
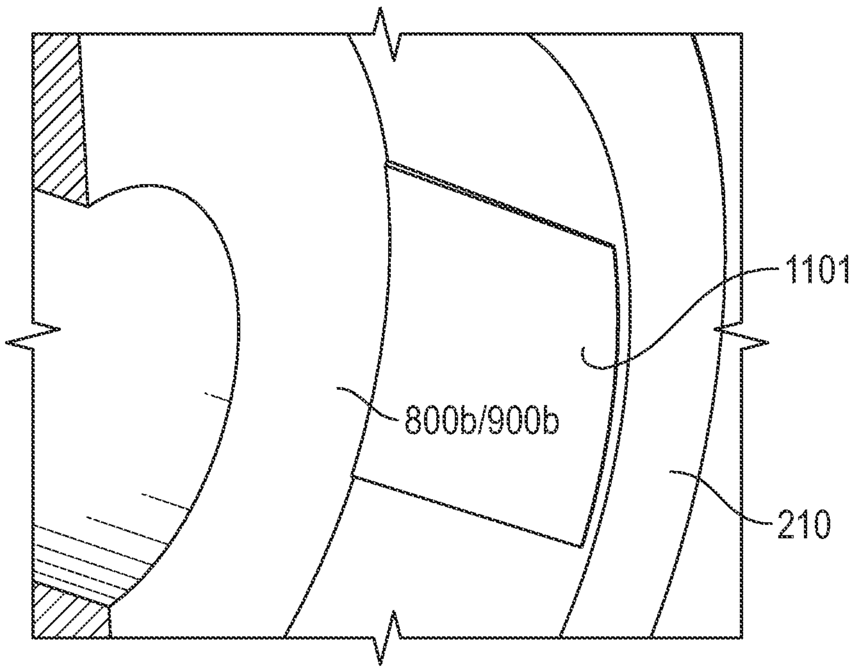
Figure 11C:
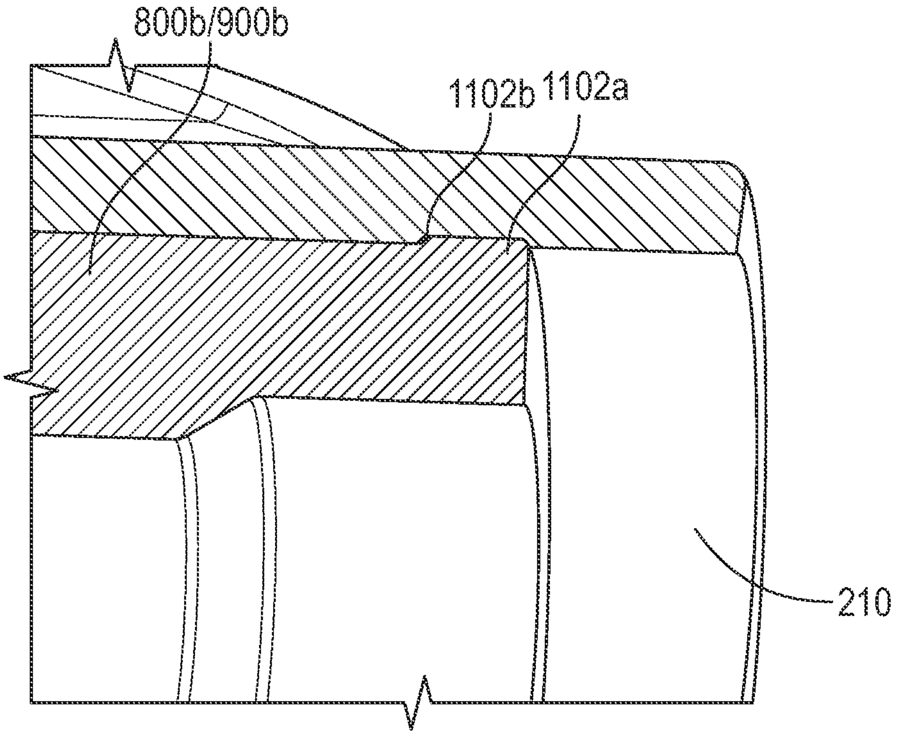

FIGS. 11A-11C each represent a different way in which path-defining structure 800 or 900 could be secured within chamber 210*b*. In FIG. 11A, opening 901 is shown as having an inner dimension that corresponds closely with the outer dimension of needle retaining portion 202*c* such that a press-fit interface is formed. Opening 801 could equally be configured in this manner. Alternatively, opening 801/901 could be molded overtop needle retaining portion 202*c*.

In FIGS. 11B and 11C, path-defining structure 800/900 can be retained within chamber 210*b* using an interface between proximal portion 800*b*/900*b* and an inner surface of chamber 210*b*. In FIG. 11B, chamber 210*b* can include a sloped retention bump 1101. The slope of bump 1101 can cause a distal facing ledge to be formed against which a proximal end of proximal portion 800*b* or 900*b* contacts. This sloping facilitates inserting path-defining structure 800 or 900 but prevents it from being later withdrawn.

FIG. 11C illustrates an example where proximal portion 800*b* or 900*b* includes a retention rib 1102*a* which inserts into a retention trench 1102*b* formed on an inner surface of chamber 210*b*. During assembly, path-defining structure 800 or 900 can be inserted into chamber 210*b* until retention rib 1102*a* inserts into retention trench 1102*b*. At this point, retention rib 1102*a* will prevent the path-defining structure from being proximally withdrawn.

Figure 12A:
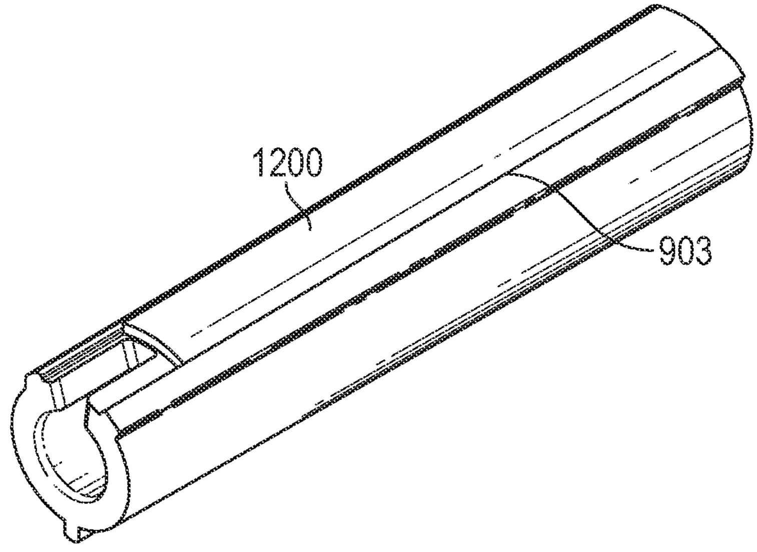
FIGS. 12A and 12B each illustrate an example of how a porous material can be included within a portion of a visualization channel of a path-defining structure.
Figure 12B:
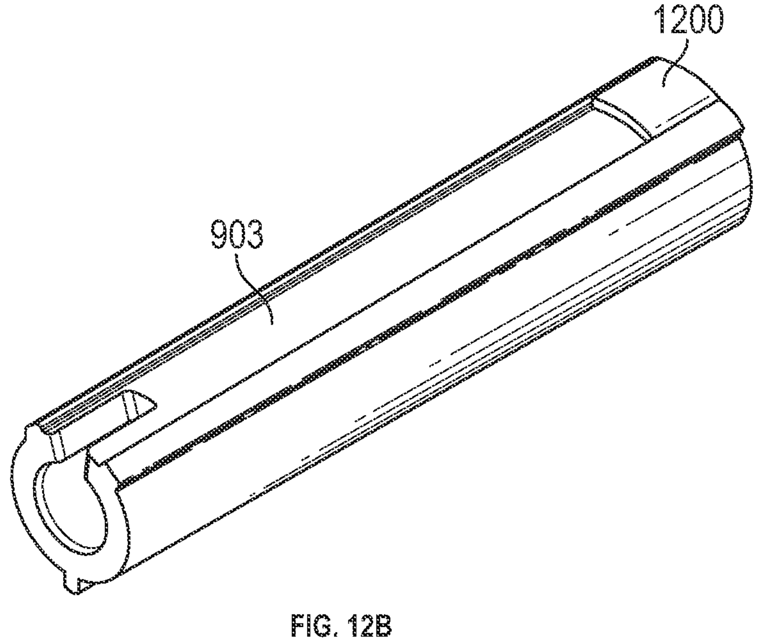

In some embodiments, a porous material could be employed within the channel created by the path-defining structure. For example, in FIG. 12A, a porous material 1200 can be fabricated into visualization channel 903 and extend through the portion of proximal portion 900*b* that includes venting grooves 902. Porous material 1200 can function to vent air while also wicking the blood at a rate that will be easily visualized. Alternatively, porous material 1200 may only be positioned within the portion of proximal portion 900*b* as shown in FIG. 12B.

Figure 13:
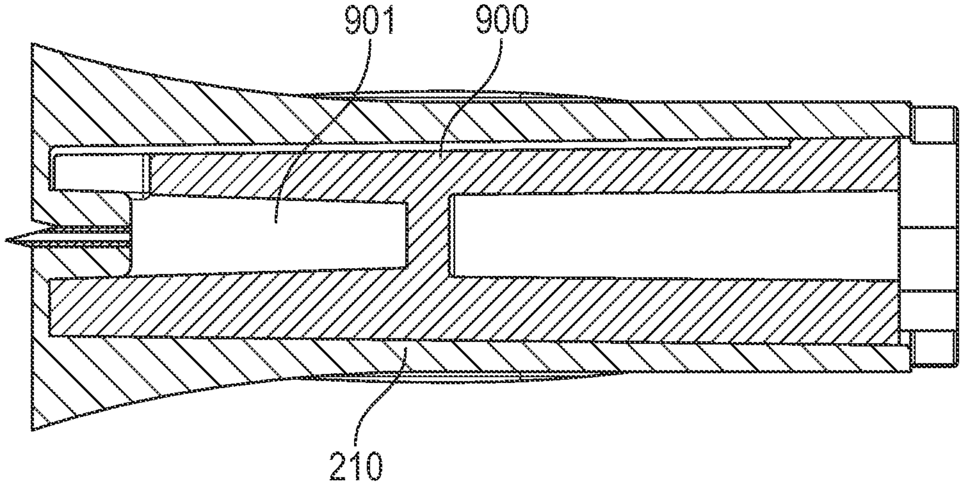
FIG. 13 illustrates how the volume of an opening in the path-defining structure can be increased to accommodate different insertion techniques.
Figure 14:
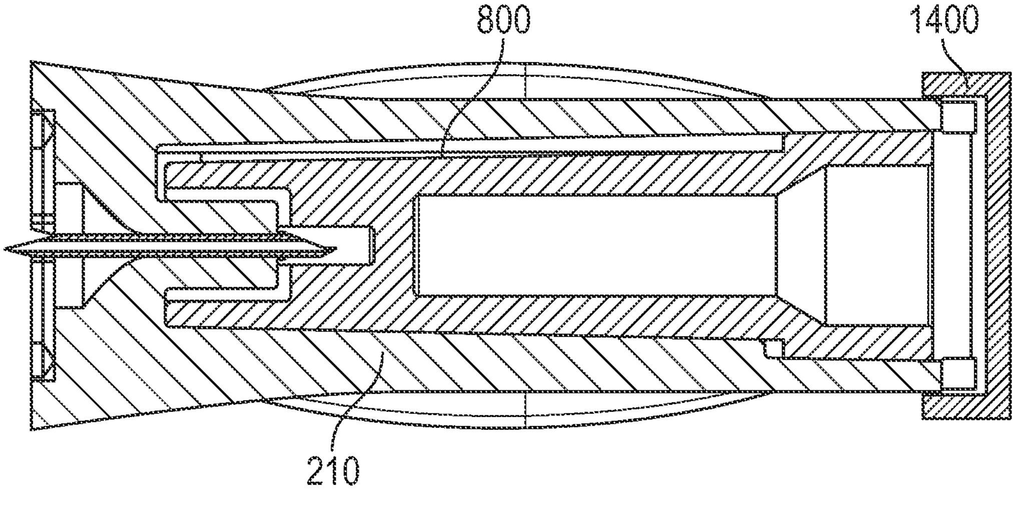
FIG. 14 illustrates how a flash chamber can include a sealing cap to accommodate different insertion techniques.

FIGS. 13 and 14 each depict additional variations that can be made to embodiments that employ either path-defining structure 800 or 900. In FIG. 13, opening 901 is shown having a larger depth. With this larger depth, more fluid volume will be required before blood will flow through the channel. Accordingly, the depth of opening 801 or 901 can be selected to generally control when visual feedback of proper vein confirmation will be provided. In FIG. 14, a sealing cap 1400 is positioned overtop the proximal opening of flash chamber 210. Sealing cap 1400 can block the flow of air until removed. Therefore, sealing cap 1400 can be employed in situations where extension tube 103 is pre-primed with saline to prevent the saline from flowing proximally into flash chamber 210. More specifically, with sealing cap 1400 in place, the saline will only be allowed to flow distally within needle 202*a*. After insertion of the needle, sealing cap 1400 can be removed to allow flash chamber 210 to be employed in the manner described above.

Various embodiments of the present invention further comprise a safety mechanism configured to secure the sharpened, distal tip of the introducer needle following removal and separation of the needle hub from the catheter adapter. A safety mechanism may include any compatible device known in the art. In some instances, the safety mechanism is configured to interact with a needle feature, such as a ferrule, notch, crimp or bump on the cannula. The crimp or bump formed in the cannula causes a slight out of round configuration that can be used to activate a safety mechanism. In some instance, the safety mechanism comprises an arm or lever that is actuated to capture the needle tip within the mechanism and prevent the tip from emerging prior to safe disposal.

The safety mechanism is attached to the body of the needle and is capable of sliding along the length thereof. In some instances, an initial or assembled position of the safety mechanism is located in proximity to the base or proximal end of the catheter adapter prior to catheterization. For some configurations, the assembled position of the safety mechanism is between the proximal end of the needle hub and the proximal end of the catheter adapter or stabilization platform, wherein the safety mechanism does not overlap the catheter adapter or stabilization platform. In some instances, a portion of the safety mechanism is positioned within the catheter adapter, with the balance of the safety mechanism being positioned external to the catheter adapter, such as within the needle hub. In some embodiments, a portion of the catheter adapter or stabilization platform is extended proximally to provide a housing in which at least a portion of the safety mechanism is housed. In some instances, the entire safety mechanism is housed within the housing of the catheter adapter or stabilization platform prior to catheterization.

In some embodiments, the assembled position of the safety mechanism positions the proximal end of the catheter adapter between the distal end of the safety mechanism and a distal end of a paddle grip of the needle hub. In some instances, the assembled position of the safety mechanism positions the proximal end of the catheter adapter between the distal end of the safety mechanism and a proximal end of a paddle grip of the needle hub. In some instances, a portion of the safety mechanism overlaps a portion of a paddle grip of the needle hub. In some embodiments, at least some portion of at least one of the catheter adapter and the paddle grip overlaps at least some portion of the safety mechanism. In some embodiments, no portion of the catheter adapter or paddle grip overlaps any portion of the safety mechanism.

In some embodiments, a defeatable mechanical connection is provided between the safety mechanism and at least one other component of the access device. In some embodiments, a distal end of the safety mechanism is selectively coupled to a proximal end of the catheter adapter. In one embodiment, the safety mechanism interlocks internally to the proximal end of the catheter adapter. In one embodiment, the safety mechanism interlocks externally to the proximal end of the catheter adapter. In some embodiments, a distal end of the safety mechanism is selectively coupled to a proximal end of the stabilization platform. In some embodiments, a surface of the safety mechanism is selectively coupled to at least one surface of at least one of the catheter adapter, a blood control valve, an extension tube, and the stabilization platform. In some instances, the mechanical connection is defeated upon securement of the needle tip within the safety mechanism.

In some embodiments, a particular catheter device, such as, for example, the catheter device of any of the FIGS. 1-14, may include a needle safety mechanism. The safety mechanism may include any safety mechanism configured to secure a sharpened, distal tip of an introducer needle when the needle is withdrawn from a catheter of the particular catheter device, preventing accidental needle sticks.

The safety mechanism may be coupled with the particular catheter device in any number of ways. In some embodiments, the safety mechanism may include an internal interlock in which the safety mechanism is coupled with an internal surface of a catheter adapter. Coupling may include threading, fitting, snapping, connecting, attaching, fastening, clipping, hooking, or any other suitable means of coupling. Non-limiting examples of safety mechanisms that include an internal interlock are provided in: U.S. Pat. No. 8,496,623, titled BI-DIRECTIONAL CANNULA FEATURE CAPTURE MECHANISM, filed Mar. 2, 2009; U.S. Pat. No. 9,399,120, titled BI-DIRECTIONAL CANNULA FEATURE CAPTURE MECHANISM, filed Jul. 11, 2013; U.S. Patent Application No. 62/314,262, titled CANNULA CAPTURE MECHANISM, filed Mar. 28, 2016, each of which is herein incorporated by reference in its entirety. In some embodiments, the safety mechanism may include a clip disposed within the catheter adapter, a non-limiting example of which is provided in U.S. Pat. No. 6,117,108, titled SPRING CLIP SAFETY IV CATHETER, filed Jun. 12, 1998, which is herein incorporated by reference in its entirety.

In some embodiments, the safety mechanism may include an external interlock in which the safety mechanism is coupled with an external surface of the catheter adapter. In some embodiments, the safety mechanism may be coupled with an external surface of the catheter adapter and an internal and/or external surface of a needle hub. Coupling may include threading, fitting, snapping, connecting, attaching, fastening, clipping, hooking, or any other suitable means of coupling. Non-limiting examples of safety mechanisms that include an external interlock are provided in U.S. Pat. No. 10,500,376, titled PORTED IV CATHETER HAVING EXTERNAL NEEDLE SHIELD AND INTERNAL BLOOD CONTROL SEPTUM, filed Jun. 4, 2014, which is herein incorporated by reference in its entirety. In some embodiments, the safety mechanism may include a V-clip or a similar clip. A non-limiting example of a V-clip is provided in U.S. Pat. No. 10,500,376, titled PORTED IV CATHETER HAVING EXTERNAL NEEDLE SHIELD AND INTERNAL BLOOD CONTROL SEPTUM, filed Jun. 4, 2014, which is herein incorporated by reference in its entirety. The V-clip may selectively retain a portion of the catheter adapter.

In some embodiments, a defeatable mechanical connection is provided between the safety mechanism and at least one other component of the IV catheter system. In some instances, the mechanical connection is defeated upon securement of the distal tip of the needle within the safety mechanism. In some embodiments, a surface of the safety mechanism is selectively coupled to one or more of the following: the catheter adapter, a blood control valve, an extension tube, and one or more paddle grips.

In some embodiments, the safety mechanism may include a safety barrel, which may be spring-loaded. For example, the safety barrel may be spring loaded as in the BD™ Insyte® Autoguard™ BC shielded protective IV catheter. In some embodiments, the safety mechanism may be passively and/or actively activated. In some embodiments, the safety mechanism may be configured to interact with a needle feature, such as a ferrule, notch, crimp or bump on the needle. In some embodiments, the safety mechanism may include an arm or lever that may be actuated to capture the distal tip within the safety mechanism and prevent the tip from emerging prior to safe disposal. In some embodiments, the safety mechanism may be attached to a body of the needle and may be capable of sliding along the length thereof.

In some embodiments, in an assembled position prior to catheterization, the safety mechanism may be disposed between the catheter adapter and the needle hub. In some embodiments, the catheter adapter and the needle hub may be spaced apart by at least a portion of the safety mechanism in the assembled position prior to catheterization. In some embodiments, in the assembled position prior to catheterization, a proximal end of the catheter adapter may be disposed between a distal end of the safety mechanism and a distal end of a grip of the needle hub, such as, for example, a paddle grip. In some embodiments, in the assembled position prior to catheterization, the proximal end of the catheter adapter body may be disposed between the distal end of the safety mechanism and a proximal end of the grip of the needle hub. In some embodiments, a portion of the safety mechanism may overlap with a portion of the grip of the needle hub. In some embodiments, at least a portion of at least one of the catheter adapter and the grip overlaps at least some portion of the safety mechanism. In some embodiments, no portion of the catheter adapter body or the grip overlaps any portion of the safety mechanism.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. An IV access device comprising:

a catheter adapter from which a catheter extends distally;

an extension tube coupled to the catheter adapter; and a needle hub from which a needle extends distally, the needle hub being coupled to the catheter adapter such that the needle extends through the catheter, the needle having a proximal end; and a path-defining structure;

wherein the needle hub further includes a flash chamber that is in fluid communication with a lumen of the needle thereby allowing blood to flow into a path within the flash chamber between the path-defining structure and the needle hub when a distal tip of the needle is contained within a patient's vein, wherein the path comprises a plurality of leaking channels configured to carry the blood from the proximal end of the needle in a distal direction and each comprising a groove in the path-defining structure, wherein the plurality of leaking channels are symmetrically spaced around an inner surface of an opening of the path-defining structure, wherein the path further comprises a top channel disposed along a top of the flash chamber and configured to carry the blood from the plurality of leaking channels in a proximal direction, wherein the path-defining structure is inserted into the flash chamber, wherein the path-defining structure and the path between the path-defining structure and the needle hub extend proximal to the proximal end of the needle.

2. The IV access device of claim 1, wherein proximal end of the needle includes an opening that is positioned within the flash chamber.

3. The IV access device of claim 2, wherein the IV access device includes a plug positioned proximal to the flash chamber, the plug venting air but blocking the flow of the blood from the flash chamber to an external environment.

4. The IV access device of claim 2, wherein the needle hub includes a needle retaining portion through which the needle extends, the opening of the needle being positioned proximal to the needle retaining portion.

5. The IV access device of claim 1, wherein the needle includes a notch positioned towards the distal tip of the needle, wherein blood flowing through the notch and into the catheter provides a first confirmation of proper catheter placement and blood flowing into the flash chamber provides second confirmation of proper catheter placement.

6. The IV access device of claim 1, wherein the catheter adapter includes a wing and the needle hub includes a paddle grip.

* * * * *